(12) United States Patent
Ogasawara et al.

(10) Patent No.: US 8,173,824 B2
(45) Date of Patent: May 8, 2012

(54) PROCESS FOR PRODUCING VITAMIN D DERIVATIVE USING CONVERGENT METHOD

(75) Inventors: Kunio Ogasawara, Miyagi (JP); Takashi Emura, Shizuoka (JP); Akira Kawase, Tokyo (JP); Koji Takano, Shizuoka (JP); Keisuke Yamamoto, Shizuoka (JP); Yoshiaki Kato, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 982 days.

(21) Appl. No.: 12/095,918

(22) PCT Filed: Dec. 4, 2006

(86) PCT No.: PCT/JP2006/324181
§ 371 (c)(1),
(2), (4) Date: Jun. 2, 2008

(87) PCT Pub. No.: WO2007/064011
PCT Pub. Date: Jun. 7, 2007

(65) Prior Publication Data
US 2010/0217020 A1    Aug. 26, 2010

(30) Foreign Application Priority Data

Dec. 2, 2005 (JP) .................. 2005-349702

(51) Int. Cl.
*C07C 401/00* (2006.01)
*C07C 35/00* (2006.01)
*C07C 233/00* (2006.01)
(52) U.S. Cl. .......... 552/653; 568/819; 564/188
(58) Field of Classification Search .................. 549/540; 552/653; 564/188; 568/819
See application file for complete search history.

(56) References Cited

U.S. PATENT DOCUMENTS
2004/0019023 A1    1/2004    Morikawa et al.

FOREIGN PATENT DOCUMENTS
| | | |
|---|---|---|
| JP | 08225480 | 9/1996 |
| JP | 09012502 | 1/1997 |
| JP | 10265453 | 10/1998 |
| WO | 0196293 | 12/2001 |

OTHER PUBLICATIONS

Barry M. Trost, et al., "New Strategy for the Total Synthesis of 1-Hydroxyvitamin D Derivatives", Department of Chemistry, Stanford University, J. Am. Chem. Soc. 1992, 114, 1924-1925.

Barry M. Trost, et al., "New Strategies for the Synthesis of Vitamin D Metabolites via Pd-Catalyzed Reactions", J. Am. Chem. Soc. 1992, 114, 9836-9845.

*Primary Examiner* — Taylor Victor Oh
(74) *Attorney, Agent, or Firm* — Browdy and Neimark, PLLC

(57) ABSTRACT

There are provided a novel process for producing [{(5Z,7E)-(1S,3R,20S)-1,3-dihydroxy-9,10-secopregna-5,7,10(19),16-tetraen-20-yl}oxy]-N-(2,2,3,3,3-pentafluoropropyl)acetamide, which process is shown in the following reaction scheme:

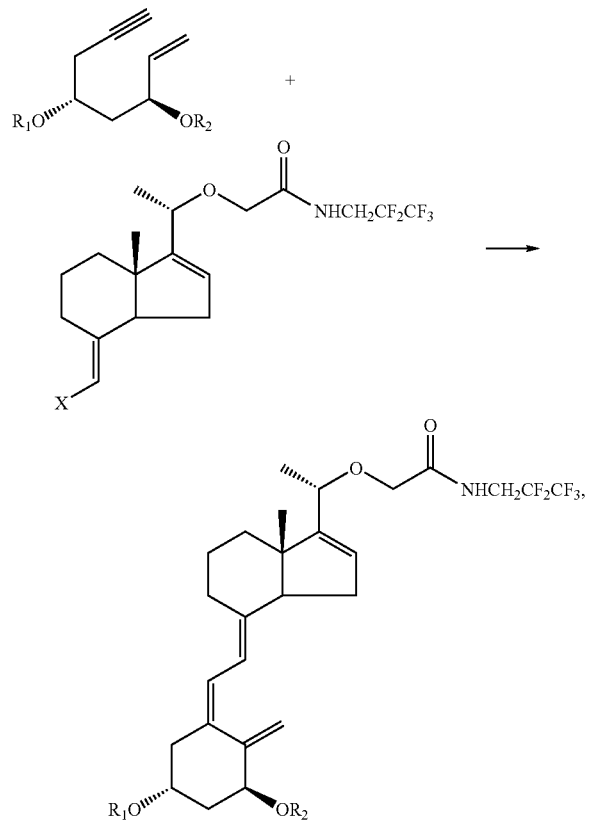

an intermediate useful for carrying out the process, and a process for producing the intermediate.

11 Claims, No Drawings

PROCESS FOR PRODUCING VITAMIN D DERIVATIVE USING CONVERGENT METHOD

TECHNICAL FIELD

The present invention relates to a novel process for producing a vitamin D derivative useful as a pharmaceutical, to an intermediate useful for carrying out the process, and to a process for producing the intermediate.

BACKGROUND ART

The vitamin D derivative represented by Formula (1):

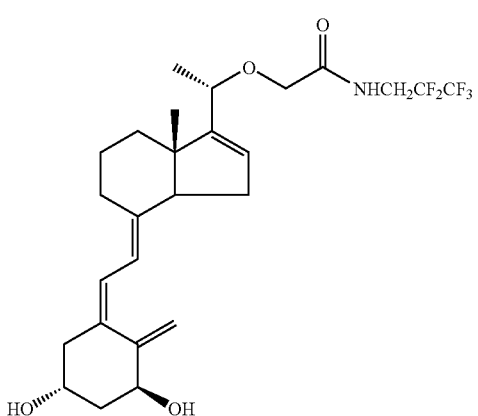

(1)

(chemical name: [{(5Z,7E)-(1S,3R,20S)-1,3-dihydroxy-9,10-secopregna-5,7,10(19),16-tetraen-20-yl}oxy]-N-(2,2,3,3,3-pentafluoropropyl)acetamide, or [{1α,3β-dihydroxy-9,10-secopregna-5,7,10(19),16-tetraen-20(S)-yl}oxy]-N-(2,2,3,3,3-pentafluoropropyl)acetamide, or N-(2,2,3,3,3-pentafluoropropyl)-[{(1S,3R,5Z,7E,20S)-1,3-dihydroxy-9,10-secopregna-5,7,10(19),16-tetraen-20-yl}oxy]acetamide) exhibits useful human keratinocyte growth inhibition activity while its harmful calcium level-raising activity is lower than the conventional vitamin D derivatives, so that it is useful as a therapeutic agent for skin disorders such as psoriasis. It is known that this compound is produced by reacting [{1α,3β-bis(tert-butyldimethylsilyloxy)-9,10-secopregna-5,7,10(19),16-tetraen-20(S)-yl}oxy]acetic acid obtained through a photoreaction using 1α,3β-dihydroxy-5-androsten-17-one as a starting material, with 2,2,3,3,3-pentafluoropropylamine (see WO 2001/096293 (Patent Literature 1)).

As examples of the synthetic method of a vitamin D derivative using a palladium catalyst, the methods described in J. Am. Chem. Soc., 1992, 114, 1924-1925 (Non-patent Literature 1), J. Am. Chem. Soc., 1992, 114, 9836-9845 (Non-patent Literature 2) and JP 9-12502 A (Patent Literature 2) are known.

As an example of deprotection of a vitamin D derivative using methanesulfonic acid, JP 8-225480 A (Patent Literature 3) is known.

Patent Literature 1: WO 2001/096293
Patent Literature 2: JP 9-12502 A
Patent Literature 3: JP 8-225480 A
Non-patent Literature 1: J. Am. Chem. Soc., 1992, 114, 1924-1925
Non-patent Literature 2: J. Am. Chem. Soc., 1992, 114, 9836-9845

DISCLOSURE OF THE INVENTION

Problems to be Solved by the Invention

However, the method described in Patent Literature 1 has drawbacks in that it is not easy to supply a large amount of 1α,3β-dihydroxy-5-androsten-17-one used as a starting material because this compound is synthesized by a special fermentation method; that a large scale production is not easy when using this starting material because a special photoreaction equipment is required for the conversion reaction from the steroid skeleton to the vitamin D skeleton; and that the overall yield is low; and so on. Thus, development of a process free from these drawbacks is desired.

The present invention was made under the above-described circumstances. Accordingly, an object of the present invention is to provide a process for producing the compound of the above-described Formula (1) which enables a large scale production of the compound.

Means for Solving the Problems

As a result of intensive research for attaining the above-described object, it has been found that the compound of Formula (1) can be efficiently produced by reacting a novel compound represented by Formula (2):

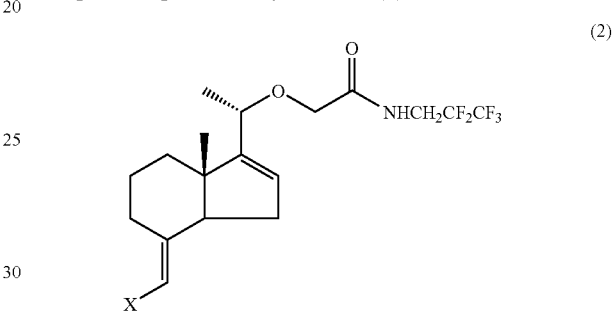

(2)

(wherein X represents a halogen atom)
with a compound represented by Formula (3):

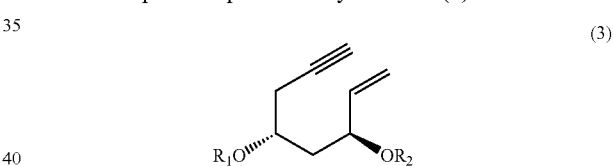

(3)

(wherein $R_1$ and $R_2$, which may be the same or different, each represent a hydrogen atom or a protective group)
in the presence of a palladium catalyst, and if desired, deprotecting the obtained compound.

Therefore, the present invention provides a process for producing the compound represented by Formula (1):

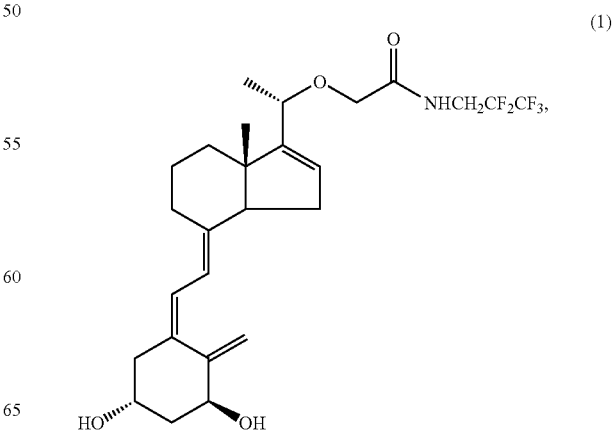

(1)

comprising the step of:
reacting a compound represented by Formula (2):

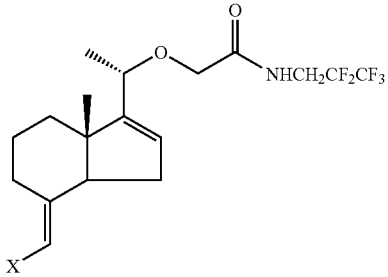

(wherein X represents a halogen atom)
with a compound represented by Formula (3):

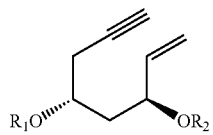

(wherein $R_1$ and $R_2$, which may be the same or different, each represent a hydrogen atom or a protective group)
in the presence of a palladium catalyst to produce a compound represented by Formula (4):

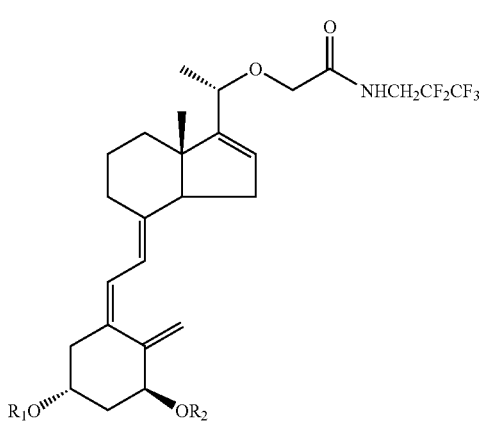

(wherein $R_1$ and $R_2$ are as defined above).

In a preferred embodiment, $R_1$ and $R_2$ are protective groups, and in this case, the process further comprises a step of deprotecting the compound of Formula (4).

To promote the reaction between the compound represented by Formula (2) and the compound represented by Formula (3), it is necessary to carry out the reaction in the presence of a palladium catalyst, using a ligand, under basic conditions, in a suitable solvent.

Examples of the palladium catalyst include palladium acetate, palladium trifluoroacetate, palladium chloride, palladium carbon, allylpalladium chloride dimer, tetrakis(triphenylphosphine)palladium, bis(dibenzylideneacetone)palladium, tris(dibenzylideneacetone)dipalladium, tris(dibenzylideneacetone)(chloroform)dipalladium, dichlorobis(triphenylphosphine)palladium, and bis(acetonitrile)dichloropalladium. Preferred examples include palladium acetate, palladium chloride, allylpalladium chloride dimer, tetrakis(triphenylphosphine)palladium, bis(dibenzylideneacetone)palladium and tris(dibenzylideneacetone)dipalladium. Especially preferred examples include palladium acetate. The catalyst may be used in the range of 0.001 to 1 equivalent with respect to the compound represented by Formula (2).

Examples of the ligand include triphenylphosphine, tri-o-tolylphosphine, tri(2-furyl)phosphine, tri-t-butylphosphine, tricyclohexylphosphine, tri-n-butylphosphine, 1,2-bis(diphenylphosphino)ethane, 1,3-bis(diphenylphosphino)propane, 1,4-bis(diphenylphosphino)butane, and 1,1'-bis(diphenylphosphino)ferrocene. Preferred examples include triphenylphosphine, tri-o-tolylphosphine, tri(2-furyl)phosphine and 1,1'-bis(diphenylphosphino)ferrocene. Especially preferred examples include triphenylphosphine.

Examples of the base used in order to carry out the reaction under basic conditions include triethylamine, diisopropylethylamine, triisopropylamine, N-methylmorpholine, N-methylpyrrolidine, N-methylpiperidine, tri-n-propylamine, tri-n-butylamine, triisobutylamine, pyridine, 2,6-lutidine, 2,4,6-collidine, N,N-dimethylaniline, N,N-diethylaniline, 1,8-diazabicyclo[5,4,0]undec-7-ene, 1,5-diazabicyclo[4,3,0]non-5-ene, 1,4-diazabicyclo[2,2,2]octane, potassium carbonate, sodium carbonate, lithium carbonate, barium carbonate, potassium hydrogen carbonate, sodium hydrogen carbonate, lithium hydrogen carbonate, potassium hydroxide, sodium hydroxide, lithium hydroxide, barium hydroxide, potassium phosphate, sodium phosphate, dipotassium hydrogen phosphate, and disodium hydrogen phosphate. Preferred examples include triethylamine, diisopropylethylamine, triisopropylamine, N-methylmorpholine, N-methylpyrrolidine, N-methylpiperidine, tri-n-propylamine, tri-n-butylamine and triisobutylamine. Especially preferred examples include triethylamine.

Examples of the suitable reaction solvent include organic solvents such as toluene, benzene, hexane, heptane, ethylbenzene, cumene, chlorobenzene, benzotrifluoride, tetrahydrofuran, 1,4-dioxane, methyl cyclopentyl ether, t-butyl methyl ether, ethyleneglycol dimethyl ether, ethyleneglycol diethyl ether, diglyme, ethyl acetate, n-propyl acetate, i-propyl acetate, n-butyl acetate, i-butyl acetate, s-butyl acetate, t-butyl acetate, acetonitrile, propionitrile, benzonitrile, dimethylformamide, dimethylacetamide, N-methylpyrrolidinone, dimethyl sulfoxide and the like, and mixed solvents thereof. Preferred examples include toluene, ethylbenzene, cumene, chlorobenzene, benzotrifluoride, tetrahydrofuran, 1,4-dioxane, t-butyl methyl ether, ethyleneglycol dimethyl ether, ethyleneglycol diethyl ether, diglyme and ethyl acetate. Especially preferred is toluene.

The reaction temperature of this reaction is preferably in the range of 0° C. to 150° C., and more preferably, for example, in the range of 80° C. to 100° C. The reaction time is usually the time until the compound of Formula (2) used as the starting material disappears. The reaction may be carried out for 0.5 to 96 hours, preferably, for example, for 8 to 10 hours.

After completion of the reaction, the compound of Formula (4) may be obtained as a crude product by evaporating the solvent; adding e.g. hexane thereto; removing the precipitates; and then evaporating the solvent under reduced pressure.

In cases where $R_1$ and $R_2$ are protective groups, the compound of Formula (1) may be obtained by deprotecting the compound of Formula (4) by a conventional method.

The protective groups of $R_1$ and $R_2$ are not restricted as long as they are protective groups of hydroxyl group. Specifically, $R_1$ and $R_2$, which are the protective groups, may be the same or different, and examples thereof include substituted silyl groups, acyl groups, optionally substituted alkyl groups, and optionally substituted tetrahydropyranyl groups. Preferably, the protective groups $R_1$ and $R_2$ each is a substituted carbonyl group or a substituted silyl group, and especially preferably a substituted silyl group.

Examples of the substituted silyl group which is a protective group represented by $R_1$ and $R_2$ include tri-substituted silyl groups such as trimethylsilyl group, triethylsilyl group, tri-i-propylsilyl group, dimethyl-i-propylsilyl group, diethyl-i-propylsilyl group, dimethylthexylsilyl group, t-butyldimethylsilyl group, t-butyldiphenylsilyl group, tribenzylsilyl group, tri-p-xylylsilyl group, triphenylsilyl group, diphenylmethylsilyl group, t-butylmethoxyphenylsilyl group and the like. Among these, trimethylsilyl group, triethylsilyl group, tri-i-propylsilyl group, dimethyl-i-propylsilyl group, diethyl-i-propylsilyl group, dimethylthexylsilyl group, t-butyldimethylsilyl group, t-butyldiphenylsilyl group, tribenzylsilyl group, tri-p-xylylsilyl group, triphenylsilyl group, diphenylmethylsilyl group and t-butylmethoxyphenylsilyl group are preferred. More preferred are triethylsilyl group, tri-i-propylsilyl group, dimethyl-i-propylsilyl group, diethyl-i-propylsilyl group, t-butyldimethylsilyl group, t-butyldiphenylsilyl group, triphenylsilyl group, and diphenylmethylsilyl group. Especially preferred is t-butyldimethylsilyl group.

Examples of the substituted carbonyl group which is a protective group represented by $R_1$ and $R_2$ include formyl group, acetyl group, chloroacetyl group, dichloroacetyl group, trichloroacetyl group, trifluoroacetyl group, methoxyacetyl group, propionyl group, butyryl group, i-butyryl group, pivaloyl group, adamantyl group, cyclohexanecarbonyl group, benzoyl group, 4-nitrobenzoyl group, 4-chlorobenzoyl group, 4-methoxybenzoyl group, naphthoyl group, toluoyl group, 9-fluorenecarbonyl group, methoxycarbonyl group, ethoxycarbonyl group, t-butoxycarbonyl group, benzyloxycarbonyl group, 4-methoxybenzyloxycarbonyl group, 9-fluorenylmethyloxycarbonyl group, 2,2,2-trichloroethoxycarbonyl group, 2-(trimethylsilyl)ethoxycarbonyl group, 2-(methylthiomethoxy)ethoxycarbonyl group, propoxycarbonyl group, isopropoxycarbonyl group, i-butoxycarbonyl group, vinyloxycarbonyl group, allyloxycarbonyl group, p-nitrophenyloxycarbonyl group, 3,4-dimethoxybenzyloxycarbonyl group, o-nitrobenzyloxycarbonyl group, p-nitrobenzyloxycarbonyl group, benzylthiocarbony, 4-ethoxy-1-naphthyloxycarbonyl group, (methylthio)thiocarbonyl group, i-butylaminocarbonyl group, and phenylaminocarbonyl group. Among these, formyl group, acetyl group, chloroacetyl group, dichloroacetyl group, trichloroacetyl group, trifluoroacetyl group, methoxyacetyl group, triphenylmethoxyacetyl group, phenoxylacetyl group, propionyl group, butyryl group, i-butyryl group, 4-(methylthiomethoxy)butyryl group, pivaloyl group, 1-adamantanecarbonyl group, cyclohexanecarbonyl group, benzoyl group, 4-nitrobenzoyl group, 4-chlorobenzoyl group, 2-iodobenzoyl group, 4-methoxybenzoyl group, p-phenylbenzoyl group, naphthoyl group, toluoyl and 9-fluorenecarbonyl group are preferred. More preferred are acetyl group, pivaloyl group, benzoyl group, and 4-methoxybenzoyl group.

Examples of the optionally substituted alkyl group which is a protective group represented by $R_1$ and $R_2$ include, typically, $C_1$-$C_{15}$ straight or branched alkyl groups and $C_3$-$C_{15}$ cyclic alkyl groups which are optionally substituted. Specifically, examples thereof include methyl group, methoxymethyl group, methylthiomethyl group, t-butylthiomethyl group, (phenyldimethylsilyl)methoxymethyl group, benzyloxymethyl group, p-methoxybenzyloxymethyl group, p-chlorobenzyloxymethyl group, (4-methoxyphenoxyl)methyl group, t-butoxymethyl group, 2-methoxyethoxymethyl group, 2,2,2-trichloroethoxymethyl group, 2-(trimethylsilyl)ethoxymethyl group, phenylthiomethyl group, cyclopropylmethyl group, 1-methoxycyclohexyl group, 1-ethoxyethyl group, methoxyisopropyl group, 1-(2-chloroethoxy)ethyl group, 1-methyl-1-methoxyethyl group, 1-methyl-benzyloxyethyl group, 1-methyl-1-benzyloxy-2-fluoroethyl group, 2,2,2-trichloroethyl group, 2-trimethylsilylethyl group, 2,2-dichloro-1,1-difluoroethyl group, t-butyl group, diphenylmethyl group, triphenylmethyl group, p-methoxyphenyldiphenylmethyl group, di(p-methoxyphenyl)phenylmethyl group, trip-methoxyphenyl)methyl group, benzyl group, p-methoxybenzyl group, 3,4-dimethoxybenzyl group, o-nitrobenzyl group, p-nitrobenzyl group, p-chlorobenzyl group, p-bromobenzyl group, 2,6-dichlorobenzyl group, p-cyanobenzyl group, p-phenylbenzyl group, 4-(dimethylaminocarbonyl)benzyl group, allyl group, 2-picolyl group, 4-picolyl group, 1,3-benzodithiolan-2-yl group, and 5-dibenzosuberyl group. Preferred are methoxymethyl group, benzyloxymethyl group, t-butyl group, diphenylmethyl group, triphenylmethyl group, benzyl group, p-methoxybenzyl group, and 3,4-dimethoxybenzyl group.

Examples of the optionally substituted tetrahydropyranyl group which is a protective group represented by $R_1$ and $R_2$ include tetrahydropyranyl group, tetrahydrothiopyranyl group, 4-methoxytetrahydropyranyl group, 4-methoxytetrahydrothiopyranyl group, 4-methoxytetrahydrothiopyranyl S,S-dioxide group and 1,4-dioxane-2-yl group. Preferred is tetrahydropyranyl group.

Examples of the optionally substituted tetrahydrofuranyl group which is a protective group represented by $R_1$ and $R_2$ include tetrahydrofuranyl group and tetrahydrothiofuranyl group.

Although $R_1$ and $R_2$ may be the same or different, $R_1$ and $R_2$ are preferably the same. More preferably, $R_1$ and $R_2$ are the same and both represent substituted silyl groups. Among these, it is especially preferred that both $R_1$ and $R_2$ are t-butyldimethylsilyl groups.

In cases where both $R_1$ and $R_2$ are substituted silyl groups, for example, deprotection of the compound of Formula (4), i.e. conversion of $R_1$ and $R_2$ to hydrogen atoms, is carried out by using an acid and a fluorine-containing reagent. Examples of the acid include inorganic acids such as hydrochloric acid, hydrobromic acid, sulfuric acid, nitric acid, phosphoric acid, and perchloric acid; and organic acids such as trifluoroacetic acid, trichloroacetic acid, methanesulfonic acid, p-toluenesulfonic acid, benzenesulfonic acid, camphorsulfonic acid, oxalic acid and citric acid, as well as an acid ion exchange resin. Examples of the fluorine-containing reagent include tetra-n-butylammonium fluoride, hydrogen fluoride/pyridine, hydrogen fluoride/triethylamine, hydrofluoric acid, lithium fluoride, sodium fluoride, potassium fluoride, cesium fluoride and the like. The solvent may be appropriately selected and, for example, solvents such as an alcoholic solvents, ether, ester, nitrile and amide solvents may be used. The reaction temperature is varied depending on the substrate, and is usually in the range of 0° C. to 120° C.

In a preferred embodiment, in cases where the protective groups of the compound of Formula (4) are substituted silyl group, an acid, preferably an inorganic acid, especially preferably hydrochloric acid is used as the reagent since it may suppress by-product formation and/or improve purity of the compound of Formula (1). The deprotection may be carried out by reacting them in an alcoholic solvent, preferably in ethanol, at room temperature for usually 1 to 30 hours.

The concentration of hydrochloric acid in the reaction system is preferably 0.5 to 5% w/w, more preferably 1 to 3% w/w, when expressed as a concentration of concentrated hydrochloric acid (25-38%) with respect to ethanol. The reaction time varies depending on the concentration of hydrochloric acid. For example, in cases where the concentration of hydrochloric acid mentioned above is 1% w/w, the reaction time is preferably 2 to 24 hours, more preferably 3 to 10 hours. In cases where the concentration of hydrochloric acid mentioned above is 1.5% w/w, the reaction time is preferably 1.5 to 10 hours, more preferably 2 to 5 hours.

After deprotection, the obtained compound of Formula (1) may be additionally purified by silica gel column chromatography. If the compound of Formula (4) wherein $R_1$ and $R_2$ are protective groups is purified preliminarily by silica gel column chromatography, the compound of Formula (1) having relatively high purity may be obtained even immediately after deprotection.

The compound represented by Formula (2) used in the above-described method is novel, thus the present invention also provides a compound of Formula (2).

In a compound of Formula (2), X is a halogen atom such as a chlorine atom, bromine atom, iodine atom and the like, and preferably a bromine atom.

Further, the present invention also provides a process for producing the compound of Formula (2).

According to the process, the compound of Formula (2) may be obtained by reacting a compound represented by Formula (5):

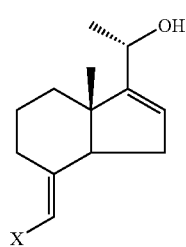

(5)

(wherein X represents a halogen atom.)
with 2-bromo-N-(2,2,3,3,3-pentafluoropropyl)acetamide in the presence of a base.

Examples of the base which may be used include metal amides such as potassium hexamethyldisilazide, sodium hexamethyldisilazide, lithium hexamethyldisilazide, lithium diisopropylamide, lithium dicyclohexylamide, lithium amide, sodium amide, potassium amide and the like; metal hydrides such as sodium hydride, potassium hydride, lithium hydride and the like; and metal alkoxides such as potassium-t-butoxide, sodium-t-butoxide, lithium-t-butoxide, potassium-t-pentoxide, sodium-t-pentoxide, lithium-t-pentoxide and the like. Preferred examples include metal amides such as potassium hexamethyldisilazide and sodium hexamethyldisilazide; metal alkoxides such as potassium-t-butoxide, sodium-t-butoxide, potassium-t-pentoxide and sodium-t-pentoxide; and metal hydrides such as sodium hydride and potassium hydride. Further, in view of avoiding side reactions, metal amides are preferable. Among these, sodium hexamethyldisilazide is more preferable. These bases may be used in the form of a solution in a solvent such as toluene, hexane or tetrahydrofuran, which solvent is unreactive to the base, and such a method is preferable.

Examples of the reaction solvent include ether solvents such as tetrahydrofuran, dioxane, ether and the like; hydrocarbon solvents such as n-pentane, n-hexane, cyclohexane, n-heptane, n-octane, toluene, xylene and the like; amide solvents such as N-methylpyrrolidone, N,N-dimethylacetamide, N,N-dimethylimidazolidinone (DMI), N,N-dimethylformamide (DMF) and the like. These solvents may be used individually or in combination, and preferably used individually except that when the solvent is used for dissolving a base. In view of avoiding side reactions and/or scaling down the reaction, preferred are amide solvents, especially N,N-dimethylformamide (DMF). Using N,N-dimethylformamide as a reaction solvent means that the reaction is carried out in N,N-dimethylformamide. The reaction temperature is usually in the range of −78° C. to 100° C., preferably −25° C. to 10° C. The reaction time is usually 5 minutes to 10 hours, preferably 10 minutes to 3 hours.

In a preferred embodiment, the desired compound may be obtained by allowing reaction of the compound of Formula (5) at −20° C. to 5° C. for 15 minutes to 1 hour in dimethylformamide by adding thereto a solution of sodium hexamethyldisilazide in tetrahydrofuran and 2-bromo-N-(2,2,3,3,3-pentafluoropropyl)acetamide.

The compound of Formula (5) used in the process for producing the compound of Formula (2) is also novel, thus the present invention further provides a compound of Formula (5).

In a compound of Formula (5), X is a halogen atom such as a chlorine atom, bromine atom, iodine atom and the like, and preferably a bromine atom.

On the other hand, the compound of Formula (3), which is reacted with the compound of Formula (2) in the process for producing the compound of Formula (1), is a known compound and may be synthesized easily by referring to, for example, Scheme 1 described below. The starting material in Scheme 1 is commercially available from Aldrich, Tokyo Chemical Industry or the like, and may be synthesized, for example, by the method described in J. Am. Chem. Soc., 1983, 105, 5925-5926. Alternatively, the compound of Formula (3) may be synthesized according to the method described in J. Chem. Soc., Chem. Commn., 1994, 16, 1903-1904; Tetrahedron Letters, 1994, 35, 8119-8122; or JP H07-145093 A.

Scheme 1:

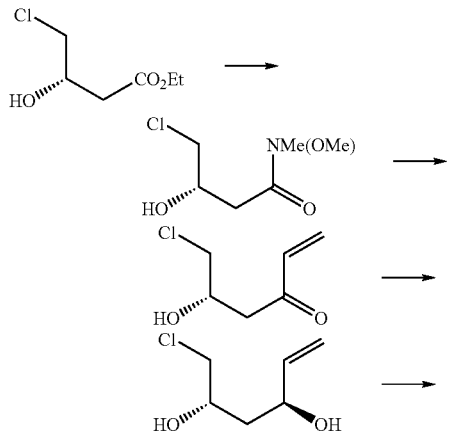

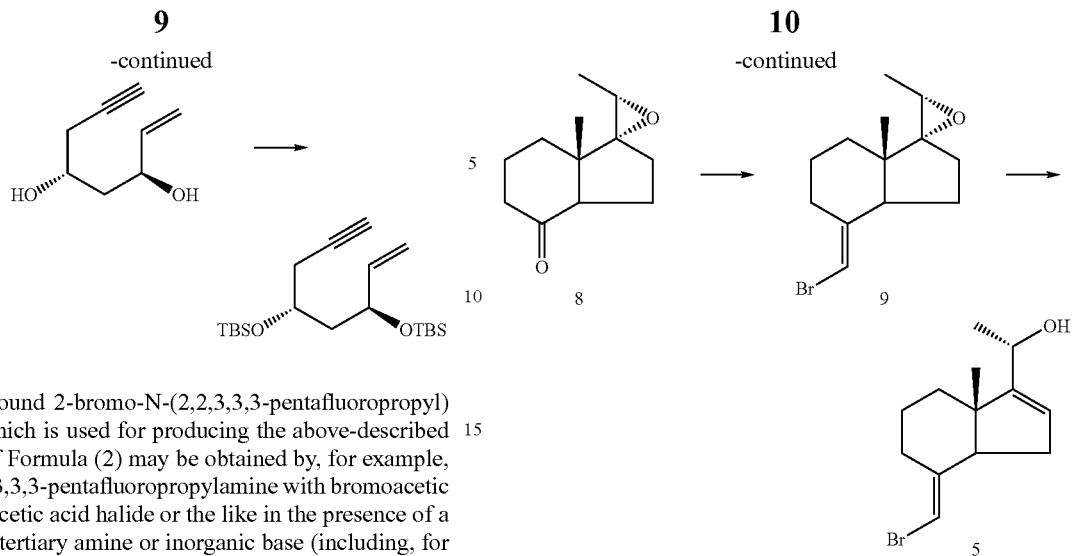

The compound 2-bromo-N-(2,2,3,3,3-pentafluoropropyl) acetamide which is used for producing the above-described compound of Formula (2) may be obtained by, for example, reacting 2,2,3,3,3-pentafluoropropylamine with bromoacetic acid, bromoacetic acid halide or the like in the presence of a base such as tertiary amine or inorganic base (including, for example, bases such as potassium hydroxide, sodium hydroxide, lithium hydroxide, potassium carbonate, sodium carbonate, lithium carbonate, potassium phosphate, sodium phosphate, lithium phosphate, N,N-dimethylaniline, N,N-diethylaniline, triethylamine, diisopropylethylamine, tri-n-butylamine, tri-n-propylamine, dicyclohexylmethylamine, N-methylmorpholine, 1,8-diazabicyclo[5.4.0]-7-undecene, pyridine, 2,6-lutidine, 2,4,6-collidine, dimethylaminopyridine and imidazole) or in the presence of a condensing agent. The reaction may be carried out in an acetic ester solvent, halogenated solvent or in an ether solvent. In cases where the halide is a bromide, 2-bromo-N-(2,2,3,3,3-pentafluoropropyl)acetamide may be easily synthesized by Scheme 2 below.

Scheme 2:

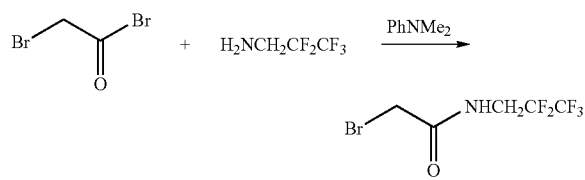

Preferably, this reaction is carried out by reacting bromoacetyl bromide with 2,2,3,3,3-pentafluoropropylamine in ethyl acetate at −20° C. to 0° C. by using N,N-dimethylaniline as a base.

The present inventors have found that the compound represented by Formula (5), which is also used for producing the compound of Formula (2), may be obtained according to the method shown in Schemes 3, 4 and 5 described below.

Scheme 3:

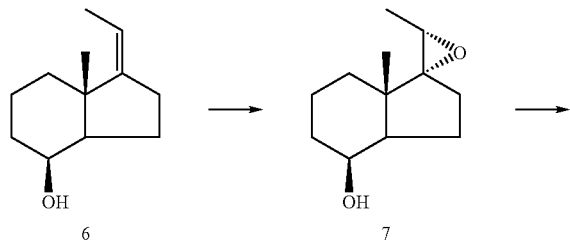

The starting material Compound 6 is a known material, and may be synthesized according to, for example, the method described in J. Org. Chem. 2001, 66, 626-628, using (S)-7a-methyl-2,3,7,7a-tetrahydro-6H-indene-1,5-dione, as a starting material, which is commercially available from ACROS, Merck and the like, or which may be synthesized, for example, according to the method described in Organic Synthesis Collect. Vol. VII, p 363-367.

Compound 7 may be obtained by epoxidizing Compound 6 by using an oxidizing agent. Examples of the oxidizing agent include perbenzoic acid, meta-chloroperbenzoic acid, p-nitroperbenzoic acid, monoperoxyphthalic acid, performic acid, peracetic acid, trifluoroperacetic acid, and peroxylauric acid. Examples of the solvent which may be used in this reaction include ethyl acetate, methyl acetate, methylene chloride, 1,2-dichloroethane, tetrahydrofuran, 1,4-dioxane, 1,2-dimethoxyethane, t-butyl methyl ether, acetonitrile, propionitrile, toluene, xylene, and chlorobenzene. The reaction temperature may usually be in the range of −50° C. to 50° C.

In a preferred embodiment, Compound 7 may be obtained by carrying out the reaction in ethyl acetate at −10° C. to 15° C. by using meta-chloroperbenzoic acid.

Compound 8 may be obtained by oxidization of the obtained Compound 7 by using an oxidizing agent. Examples of the oxidation method include a method in which a catalytic amount of tetra-n-propylammonium perruthenate is used in the presence of N-methylmorpholine-N-oxide; method in which an oxidizing agent such as N-chlorosuccinimide or sodium hypochlorite is used in the presence of a catalytic amount of 2,2,6,6-tetramethyl-1-piperidinyloxy free radical, 4-acetamido-2,2,6,6-tetramethyl-1-piperidinyloxy free radical, or 4-methoxy-2,2,6,6-tetramethyl-1-piperidinyloxy free radical; or a method in which a catalytic amount of trichlororuthenium or ruthenium oxide is used in the presence of sodium hypochlorite or peracetic acid. The catalyst may be used in the range of 0.001 to 0.5 equivalents with respect to Compound 7. Examples of the solvent which may be used in this reaction include ethyl acetate, methyl acetate, methylene chloride, dichloroethane, tetrahydrofuran, dioxane, dimethoxyethane, t-butyl methyl ether, acetonitrile, propionitrile, toluene, xylene, and chlorobenzene, preferably acetonitrile and propionitrile. The reaction temperature is usually in the range of −20° C. to 100° C.

In a preferred embodiment, Compound 8 may be obtained by carrying out the reaction in acetonitrile, adding a catalytic amount of tetra-n-propylammonium perruthenate, at room temperature in the presence of N-methylmorpholine-N-oxide.

Thereafter, Compound 9 may be obtained by reacting Compound 8 with a phosphorus ylide which has been obtained by reacting bromomethyltriphenylphosphonium bromide with a base. Examples of the base which may be used in this reaction include metal amides such as potassium hexamethyldisilazide, sodium hexamethyldisilazide, lithium hexamethyldisilazide, lithium diisopropylamide, lithium dicyclohexylamide, lithium amide, sodium amide, potassium amide and the like; metal hydrides such as sodium hydride, potassium hydride, lithium hydride and the like; and metal alkoxides such as potassium-t-butoxide, sodium-t-butoxide, lithium-t-butoxide, potassium-t-pentoxide, sodium-t-pentoxide, lithium-t-pentoxide and the like. In view of reducing the cost of the reaction and/or reducing an amount of a base and bromomethyltriphenylphosphonium bromide used and/or in view of the ease of purification of Compound 9, preferably metal alkoxide, more preferably potassium t-pentoxide may be used. An amount of the base and bromomethyltriphenylphosphonium bromide used is usually 1 to 10 equivalents, preferably 1 to 2 equivalents with respect to Compound 8. Examples of the solvent include ethyl acetate, methyl acetate, methylene chloride, dichloroethane, tetrahydrofuran, dioxane, dimethoxyethane, t-butyl methyl ether, acetonitrile, propionitrile, toluene, xylene and chlorobenzene, preferably toluene. The reaction temperature is usually −50° C. to 50° C., preferably −20° C. to 20° C. when phosphorus ylide is prepared, and is usually −78° C. to 50° C., preferably −30° C. to 0° C. when phosphorus ylide and Compound 8 are reacted.

In a preferred embodiment, Compound 9 may be obtained by reacting phosphorus ylide, which has been prepared by using 1.0-1.6 equivalents, preferably 1.2-1.5 equivalents of potassium t-pentoxide with respect to Compound 8 and 1.0-1.6 equivalents, preferably 1.2-1.5 equivalents of bromomethyltriphenylphosphonium bromide with respect to Compound 8, with Compound 8 at −25° C. to −5° C. for 15 minutes to 2 hours, preferably for 30 minutes to 2 hours.

Therefore, the present invention further provides a process for producing Compound 9.

Compound 5 may be obtained by subjecting the obtained Compound 9 to ring-opening reaction of epoxy group in the presence of an acid. Examples of the acid which may be used in this reaction include protonic acids such as formic acid, acetic acid, oxalic acid, maleic acid, fumaric acid, methanesulfonic acid, benzenesulfonic acid, p-toluenesulfonic acid, succinic acid, malonic acid, citric acid, gluconic acid, mandelic acid, benzoic acid, salicylic acid, trifluoroacetic acid, tartaric acid, propionic acid, glutaric acid, hydrochloric acid, hydrobromic acid, hydroiodic acid, sulfuric acid and phosphoric acid; and Lewis acids such as aluminum tri-i-propoxide, aluminum tri-t-butoxide, aluminum triethoxide, titanium tetra-i-propoxide, titanium tetra-n-propoxide, titanium tetraethoxide, titanium tetra-t-butoxide, trimethylsilyl trifluoromethanesulfonate, triethylsilyl trifluoromethanesulfonate, boron trifluoride etherate, boron trifluoride tetrahydrofuran complex, titanium tetrachloride, aluminum chloride, magnesium trifluoromethanesulfonate, copper trifluoromethanesulfonate, silver trifluoromethanesulfonate, titanium trifluoromethanesulfonate, aluminum trifluoromethanesulfonate, yttrium trifluoromethanesulfonate, scandium trifluoromethanesulfonate, lanthanum trifluoromethanesulfonate, samarium trifluoromethanesulfonate and cerium trifluoromethanesulfonate. Examples of the solvent include ethyl acetate, methyl acetate, methylene chloride, dichloroethane, tetrahydrofuran, dioxane, dimethoxyethane, t-butyl methyl ether, acetonitrile, propionitrile, toluene, xylene and chlorobenzene. The reaction temperature is usually in the range of 0 to 150° C. In a preferred embodiment, Compound 5, which is the desired compound represented by Formula (5), may be obtained by refluxing in toluene in the presence of aluminum tri-i-propoxide.

Scheme 3:

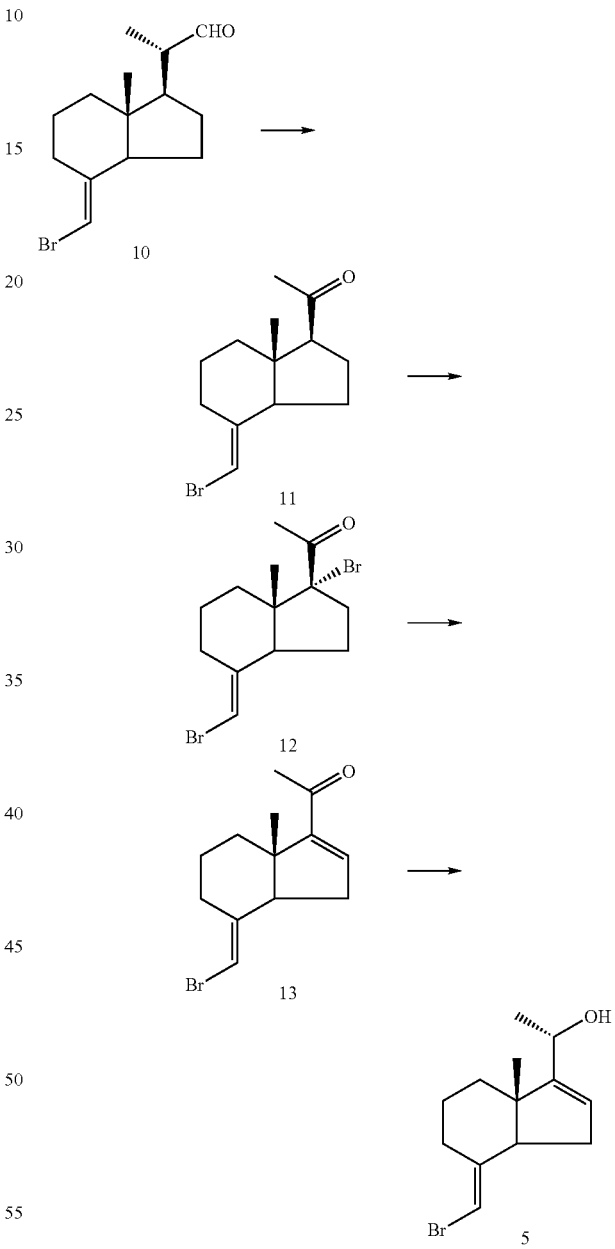

The starting material of this method, Compound 10, is a known material and may be synthesized by, for example, using vitamin D2 as a source material, in accordance with the method described in Org. Lett. 2003, 5, 4859-4862. Compound 11 may be obtained by subjecting Compound 10 to the oxidation using a suitable ligand for copper and a base under oxygen gas flow in the presence of a copper catalyst. Examples of the copper catalyst which may be used in this reaction include copper(II) acetate, copper(II) chloride, copper(II) bromide, copper(II) fluoride, copper(II) acetylacetonate, copper(I) acetate, copper(I) chloride, copper(I) bromide, copper(I) fluoride, copper(I) iodine, copper(I) cyanide, copper(II) trifluoroacetate, copper(II) trifluoromethanesulfonate, copper(I) trifluoromethanesulfonate, and copper (II) tetrafluoroborate. The catalyst may be used in the range of 0.001 to 0.5 equivalents with respect to Compound 10. Examples of the ligand which may be used include bipyridyl, 4,4'-dimethyl-2,2'-bipyridyl, 6,6'-bi-2-picoline, 1,10-phenanthroline, neocuproine and the like. Examples of the base which may be used include 1,4-diazabicyclo[2.2.2]octane, N,N-dimethylaniline, N,N-diethylaniline, triethylamine, diisopropylethylamine, tri-n-butylamine, tri-n-propylamine, dicyclohexylmethylamine, N-methylmorpholine, 1,8-diazabicyclo[5.4.0]-7-undecene, pyridine, 2,6-lutidine, 2,4,6-collidine, dimethylaminopyridine and imidazole. Examples of the solvent which may be used include dimethylformamide, dimethylacetamide, dimethylimidazolidinone, N-methylpyrrolidinone, dimethyl sulfoxide, acetonitrile, tetrahydrofuran, ethyl acetate and the like. The reaction is usually carried out in such a solvent at 0 to 150° C. In a preferred embodiment, Compound 11 may be obtained by carrying out the reaction at 60 to 100° C. in DMF under oxygen gas flow using copper(II) acetate, bipyridyl and 1,4-diazabicyclo [2.2.2]octane.

Thereafter, Compound 12 may be obtained by silylating Compound 11 with a silylating agent in the presence of a suitable base, and then by brominating the obtained silyl compound by using a suitable brominating agent in the presence of a base. Examples of the silylating agent include iodotrimethylsilane, bromotrimethylsilane, trimethylchlorosilane, trimethylsilyl trifluoromethanesulfonate, trimethylsilyl methanesulfonate, trimethylsilyl benzenesulfonate and trimethylsilyl toluenesulfonate. Examples of the base which may be used include hexamethyldisilazane, N,N-dimethylaniline, N,N-diethylaniline, triethylamine, diisopropylethylamine, tri-n-butylamine, tri-n-propylamine, dicyclohexylmethylamine, N-methylmorpholine, 1,8-diazabicyclo[5.4.0]-7-undecene, pyridine, 2,6-lutidine, 2,4,6-collidine, dimethylaminopyridine and imidazole. Examples of the solvent which may be used include methylene chloride, chloroform, toluene, ethyl acetate, tetrahydrofuran, t-butyl methyl ether, diisopropyl ether and acetonitrile. The reaction temperature is usually in the range of −50 to 100° C. Examples of the base which may be used in the brominating step include N,N-dimethylaniline, N,N-diethylaniline, triethylamine, diisopropylethylamine, tri-n-butylamine, tri-n-propylamine, dicyclohexylmethylamine, N-methylmorpholine, 1,8-diazabicyclo[5.4.0]-7-undecene, pyridine, 2,6-lutidine, 2,4,6-collidine, dimethylaminopyridine and imidazole. Examples of the brominating agent include tetra-n-butylammonium tribromide, bromine, N-bromosuccinimide, dimethyldibromohydantoin and copper(II) bromide. In a preferred embodiment, Compound 12 may be obtained by reacting Compound 11 with hexamethyldisilazane and iodotrimethylsilane at 0 to 40° C. in methylene chloride, adding saturated aqueous sodium bicarbonate to the reaction mixture, extracting the resulting mixture with hexane, evaporating hexane and reacting the remaining mixture with tetra-n-butylammonium tribromide at room temperature in a solvent such as tetrahydrofuran in the presence of triethylamine.

Compound 13 may be obtained by carrying out the dehydrobromination reaction of the obtained Compound 12 using a base and a suitable inorganic salt. As the base, potassium hydroxide, sodium hydroxide, lithium hydroxide, potassium carbonate, sodium carbonate, lithium carbonate, potassium phosphate, sodium phosphate, lithium phosphate and the like may be used. Examples of the inorganic salt include lithium bromide, sodium bromide, potassium bromide, magnesium bromide, barium bromide, lithium iodide, sodium iodide, potassium iodide, magnesium iodide, barium iodide, lithium chloride, sodium chloride, potassium chloride, magnesium chloride, and barium chloride. As the solvent, dimethylformamide, dimethylacetamide, dimethylimidazolidinone, N-methylpyrrolidinone, dimethyl sulfoxide, acetonitrile, tetrahydrofuran and the like may be used. The reaction temperature is usually in the range of 0 to 150° C. In a preferred embodiment, Compound 13 may be obtained by adding lithium bromide and lithium carbonate to Compound 12, and allowing the mixture to react in dimethylformamide at 80 to 120° C.

Thereafter, Compound 5 may be obtained by reduction of Compound 13 with a suitable reducing agent in the presence of a catalytic amount of (R)-2-methyl-CBS-oxazaborolidine. The catalyst may be used in the range of 0.001 to 0.5 equivalents with respect to Compound 13. Examples of the reducing agent include borane dimethyl sulfide complex, borane tetrahydrofuran complex, borane pyridine complex, borane dimethylaniline complex, borane diethylaniline complex, borane triethylamine complex, catechol borane, pinacol borane, 9-BBN, and dicyclohexyl borane. As the solvent, toluene, xylene, chlorobenzene, cyclohexane, hexane, heptane, dichloromethane, 1,2-dichloroethane, chloroform, t-butyl methyl ether, tetrahydrofuran, diisopropyl ether, and ethyl acetate may be used. The reaction temperature is usually in the range of −50 to 50° C. In a preferred embodiment, Compound 5, which is the desired compound represented by Formula (5), may be obtained by allowing reaction with borane dimethyl sulfide complex at 0 to 30° C. in a solvent such as toluene in the presence of a catalytic amount of (R)-2-methyl-CBS-oxazaborolidine.

Compound 9 used in Scheme 3 may also be obtained by Scheme A or B described below.

Scheme A:

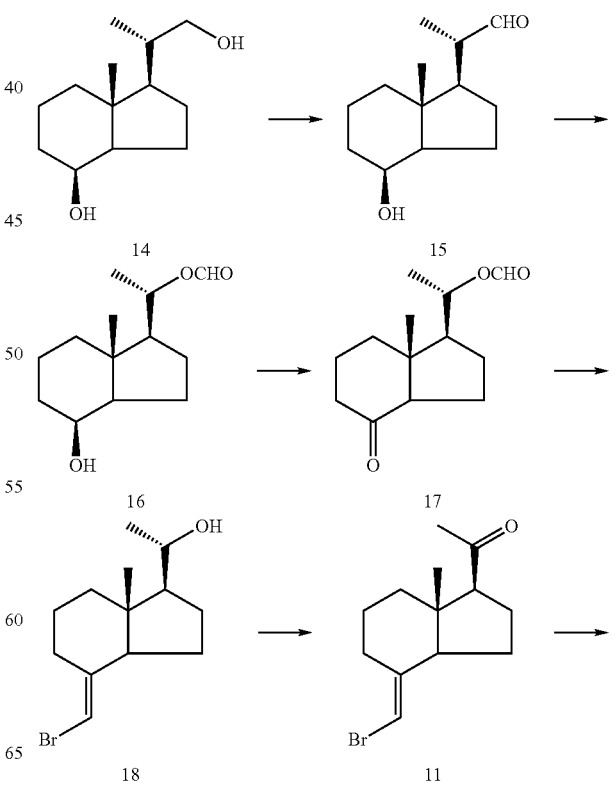

-continued

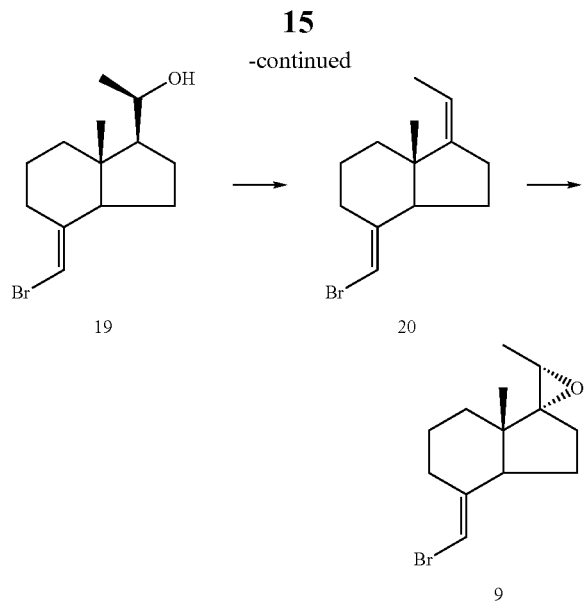

The starting material, Compound 14, is a known material and may be synthesized by, for example, using vitamin D2 as a source material, in accordance with the method described in J. Org. Chem. 1986, 51, 1264-1269. Compound 15 may be obtained by reacting Compound 14 with N-chlorosuccinimide at e.g. 0 to 30° C. in a solvent such as methylene chloride in the presence of tetrabutylammonium chloride, sodium hydrogen carbonate, potassium carbonate, and 4-acetamido-2,2,6,6-tetramethyl-1-piperidinyloxy free radical which is present in a catalytic amount of 0.001 to 0.3 equivalents with respect to Compound 14. Compound 15 is also a known material and may be synthesized according to, for example, the method described in Eur. J. Org. Chem. 1999, 9, 2241-2248.

Compound 16 may be obtained by oxidization of Compound 15 with a suitable peroxide. Examples of the peroxide which may be used include meta-chloroperbenzoic acid, perbenzoic acid, magnesium monoperoxyphthalate, peracetic acid, trifluoroperacetic acid, tert-butylhydroperoxide, oxone, and hydrogen peroxide. Examples of the solvent include toluene, xylene, chlorobenzene, cyclohexane, hexane, heptane, dichloromethane, 1,2-dichloroethane, chloroform, t-butyl methyl ether, tetrahydrofuran, diisopropyl ether, and ethyl acetate. The reaction temperature is usually in the range of −50 to 100° C. In a preferred embodiment, Compound 16 may be obtained by allowing reaction with peroxide such as meta-chloroperbenzoic acid at 0 to 40° C. in dichloromethane.

Thereafter, Compound 17 may be obtained by oxidization of Compound 16 with an oxidizing agent. Examples of the oxidation method include a method in which a catalytic amount of tetra-n-propylammonium perruthenate is used in the presence of N-methylmorpholine-N-oxide; method in which an oxidizing agent such as N-chlorosuccinimide or sodium hypochlorite is used in the presence of a catalytic amount of 2,2,6,6-tetramethyl-1-piperidinyloxy free radical, 4-acetamido-2,2,6,6-tetramethyl-1-piperidinyloxy free radical, or 4-methoxy-2,2,6,6-tetramethyl-1-piperidinyloxy free radical; or a method in which a catalytic amount of trichlororuthenium is used in the presence of sodium hypochlorite. The catalyst may be used in the range of 0.001 to 0.5 equivalents with respect to Compound 16. In a preferred embodiment, Compound 17 may be obtained by adding a catalytic amount of tetra-n-propylammonium perruthenate to Compound 16 present in acetonitrile and allowing the mixture to react at room temperature in the presence of N-methylmorpholine-N-oxide.

Compound 18 may be obtained by reacting the obtained Compound 17 with phosphorus ylide, which has been synthesized from bromomethyltriphenylphosphonium bromide and a suitable base, and subjecting the obtained compound to acid hydrolysis. Examples of the base used in the synthesis of phosphorus ylide include potassium hexamethyldisilazide, sodium hexamethyldisilazide, lithium hexamethyldisilazide, lithium diisopropylamide, lithium dicyclohexylamide, lithium amide, sodium amide, potassium amide, sodium hydride, potassium hydride, lithium hydride, potassium-t-butoxide, sodium-t-butoxide, lithium-t-butoxide, potassium-t-pentoxide, sodium-t-pentoxide, and lithium-t-pentoxide. Examples of the solvent include toluene, xylene, heptane, hexane, pentane, dichloromethane, chlorobenzene, dichloroethane, chloroform, di-i-propyl ether, cyclopentyl methyl ether, t-butyl methyl ether, tetrahydrofuran, dimethoxyethane, dioxane, and ethyl acetate. The reaction temperature is usually in the range of −50 to 100° C. Examples of the acid which may be used in acid hydrolysis include sulfuric acid, hydrochloric acid, hydrobromic acid, hydroiodic acid, phosphoric acid, methanesulfonic acid, benzenesulfonic acid, p-toluenesulfonic acid, trifluoroacetic acid, and trifluoromethanesulfonic acid. Examples of the solvent include methanol, ethanol, n-propanol, i-propanol, n-butanol, ether, tetrahydrofuran, dioxane, dimethoxyethane, acetonitrile, ethyl acetate, acetic acid, trifluoroacetic acid, and nitromethane. The reaction temperature is usually in the range of −50 to 100° C. In a preferred embodiment, Compound 18 may be obtained by reacting Compound 17 with phosphorus ylide, which has been synthesized from bromomethyltriphenylphosphonium bromide and potassium hexamethyldisilazide, at 0 to 60° C. in toluene, and then reacting the obtained compound with sulfuric acid at a concentration of 30-70% at 10 to 40° C. in dioxane.

Thereafter, Compound 11 may be obtained by oxidization of Compound 18 with an oxidizing agent. The reaction temperature is usually in the range of −50 to 100° C. Examples of the oxidation condition which may be used include a method in which a catalytic amount of tetra-n-propylammonium perruthenate is used in the presence of N-methylmorpholine-N-oxide; a method in which an oxidizing agent such as N-chlorosuccinimide or sodium hypochlorite is used in the presence of a catalytic amount of 2,2,6,6-tetramethyl-1-piperidinyloxy free radical, 4-acetamido-2,2,6,6-tetramethyl-1-piperidinyloxy free radical, or 4-methoxy-2,2,6,6-tetramethyl-1-piperidinyloxy free radical; or a method in which a catalytic amount of trichlororuthenium is used in the presence of sodium hypochlorite; or oxidation conditions where such as manganese compound, chromic acid, lead compound, mercuric compound, ozone, hydrogen peroxide, organic peroxide, organic peracid, peroxomonosulfuric acid, nitroxide, dimethyl sulfoxide, quinone, or triisopropyloxyaluminum or tri-t-butyloxyaluminum or triphenoxyaluminum-cyclohexanone or acetone is present. The reaction temperature is usually in the range of −50 to 100° C. In a preferred embodiment, Compound 11 may be obtained by allowing Compound 18 to react in a solvent such as acetonitrile in the presence of N-methylmorpholine-N-oxide by adding thereto tetra-n-propylammonium perruthenate in a catalytic amount of 0.001 to 0.3 equivalents with respect to Compound 18 at room temperature.

Compound 19 may be obtained by reduction of the obtained Compound 11. Examples of the reducing agent include lithium aluminum hydride, lithium trimethoxyaluminum hydride, lithium tri-t-butoxyaluminum hydride, lithium aluminum hydride-trichloroaluminum (alane), lithium aluminum hydride-boron trifluoride, chloromagnesium aluminum hydride, magnesium aluminum hydride, sodium aluminum hydride, sodium triethoxyalminum hydride, sodium bis (methoxyethoxy)aluminum hydride, sodium borohydride, sodium borohydride-palladium/carbon, sodium thionoboron hydride, sodium cyanoborohydride, sodium trimethoxyborohydride, lithium borohydride, lithium cyanoborohydride, lithium triethylborohydride, lithium tri-s-butylborohydride, lithium tri-t-butylborohydride, calcium borohydride, potassium borohydride, potassium triisopropoxyborohydride, potassium tri-s-butylborohydride, zinc borohydride, tetramethylammonium borohydride, tetra-n-butylammonium cyanoborohydride, diborane, dimethyl amine-borane, trimethylamine-borane, ethylenediamine-borane, pyridine-borane, dimethyl sulfide-borane, 2,3-dimethyl-2-butyl borane (thexylborane), bis-3-methyl-2-butyl borane (disiamylborane), diisopinocampheylborane, dicyclohexyl borane, and 9borabicyclo[3.3.1]nonane (9-BBN). Examples of the solvent include ether, tetrahydrofuran, dioxane and dimethoxyethane. The reaction temperature is usually in the range of −50 to 100° C. In a preferred embodiment, Compound 19 may be obtained by reacting Compound 11 with lithium tri-s-butylborohydride at e.g. −30 to 0° C. in the solvent such as tetrahydrofuran.

Compound 20 may be obtained by subjecting the obtained Compound 19 to dehydration reaction. Examples of the reaction condition which may be used in this case include a condition in which an azodicarboxylic acid derivative is used in the presence of phosphine. Examples of the phosphine include triphenylphosphine, tri-o-tolylphosphine, tri-p-tolylphosphine, tri-m-tolylphosphine, tri-n-propylphosphine, tri-n-butylphosphine, tri-i-propylphosphine, tri-i-butylphosphine, tri-s-butylphosphine, triethylphosphine, trimethylphosphine, tri-n-pentylphosphine, tri-n-hexylphosphine, tri-n-heptylphosphine, and tri-n-octylphosphine. Examples of the azodicarboxylic acid derivative include dimethyl azodicarboxylate, diethyl azodicarboxylate, di-n-propyl azodicarboxylate, di-i-propyl azodicarboxylate, di-n-butyl azodicarboxylate, di-n-pentyl azodicarboxylate, di-n-hexyl azodicarboxylate, di-n-heptyl azodicarboxylate, di-n-octyl azodicarboxylate, di-n-propyl azodicarboxylate, azodicarbonyl dipiperidine, azodicarbonyl dipyrrolidine, azodicarbonyl di-(N,N-dimethylamine), and azodicarbonyl di-(N,N-diethylamine). Examples of the solvent include toluene, xylene, heptane, hexane, pentane, dichloromethane, chlorobenzene, dichloroethane, chloroform, di-i-propyl ether, cyclopentyl methyl ether, t-butyl methyl ether, tetrahydrofuran, dimethoxyethane, dioxane, methyl acetate, ethyl acetate, acetonitrile, dimethylformamide, dimethylacetamide, and dimethyl sulfoxide. The reaction temperature is usually in the range of −50 to 100° C. In a preferred embodiment, Compound 20 may be obtained by allowing reaction with azodicarboxylic acid dimethyl ester at room temperature in tetrahydrofuran in the presence of triphenylphosphine.

Thereafter, Compound 9 may be obtained by oxidization of Compound 20 with an epoxidizing agent. Examples of the epoxidizing agent which may be used include perbenzoic acid, meta-chloroperbenzoic acid, p-nitroperbenzoic acid, monoperoxyphthalic acid, performic acid, peracetic acid, trifluoroperacetic acid, and peroxylauric acid. As the solvent, toluene, xylene, heptane, hexane, pentane, dichloromethane, chlorobenzene, dichloroethane, chloroform, di-i-propyl ether, cyclopentyl methyl ether, t-butyl methyl ether, tetrahydrofuran, dimethoxyethane, dioxane, methyl acetate, ethyl acetate, or acetonitrile may be used. The reaction temperature is usually in the range of −50° C. to 100° C. In a preferred embodiment, Compound 9 may be obtained by allowing reaction with meta-chloroperbenzoic acid at −10 to 10° C. in ethyl acetate.

Compound 11 generated in Scheme A may be used in the above-described Scheme 4 to obtain Compound 5.

Scheme B:

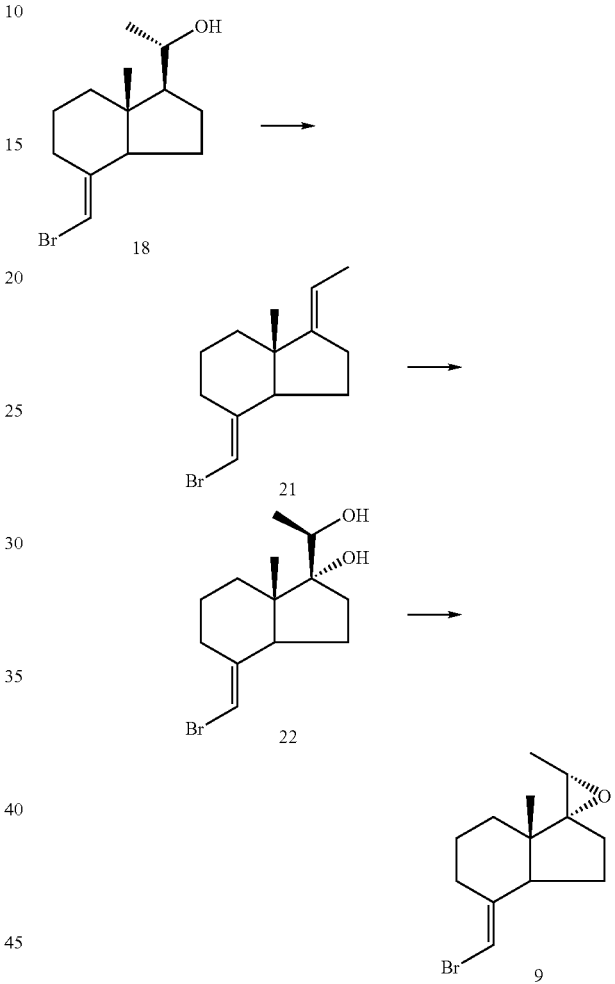

Compound 21 may be obtained by subjecting Compound 18 in Scheme A to dehydration reaction. Examples of the reaction condition which may be used in this case include a condition in which an azodicarboxylic acid derivative is used in the presence of a phosphine. Examples of the phosphine include triphenylphosphine, tri-o-tolyphosphine, tri-p-tolylphosphine, tri-m-tolylphosphine, tri-n-propylphosphine, tri-n-butylphosphine, tri-i-propylphosphine, tri-i-butylphosphine, tri-s-butylphosphine, triethylphosphine, trimethylphosphine, tri-n-pentylphosphine, tri-n-hexylphosphine, tri-n-heptylphosphine, and tri-n-octylphosphine. Examples of the azodicarboxylic acid derivative include dimethyl azodicarboxylate, diethyl azodicarboxylate, di-n-propyl azodicarboxylate, di-i-propyl azodicarboxylate, di-n-butyl azodicarboxylate, di-n-pentyl azodicarboxylate, di-n-hexyl azodicarboxylate, di-n-heptyl azodicarboxylate, di-n-octyl azodicarboxylate, di-n-propyl azodicarboxylate, azodicarbonyl dipiperidine, azodicarbonyl dipyrrolidine, azodicarbonyl di-(N,N-dimethylamine), and azodicarbonyl di-(N,N-diethylamine). Examples of the solvent include toluene, xylene, heptane, hexane, pentane, dichloromethane, chlorobenzene, dichloroethane, chloroform, di-i-propyl ether, cyclopentyl methyl ether, t-butyl methyl ether, tetrahydrofuran, dimethoxyethane, dioxane, methyl acetate, ethyl acetate, acetonitrile, dimethylformamide, dimethylacetamide, and dimethyl sulfoxide. The reaction temperature is usually in the range of −50 to 100° C. In a preferred embodiment, Compound 21 may be obtained by allowing Compound 18 to react with azodicarboxylic acid diethyl ester at room temperature in tetrahydrofuran in the presence of triphenylphosphine.

Compound 22 may be obtained by oxidization of the obtained Compound 21 with a catalytic amount of osmium compound. Examples of the osmium compound which may be used include osmium tetroxide, potassium osmate, sodium osmate, and AD-mix-α or AD-mix-β which contains osmium compound. The catalyst may be used in the range of 0.0001 to 0.5 equivalents with respect to Compound 21. Examples of the solvent include bilayer systems composed of methanol, ethanol, n-propanol, i-propanol, n-butanol, i-butanol, s-butanol, t-butanol, n-amyl alcohol, i-amyl alcohol, s-amyl alcohol, t-amyl alcohol, cyclohexanol, cyclopropanol and water. The reaction temperature is usually in the range of −50 to 100° C. In a preferred embodiment, Compound 22 may be obtained by reacting Compound 21 with AD-mix-α commercially available from Aldrich at room temperature in a mixed solvent of t-butanol and water in the presence of methanesulfonamide (see, such as J. Org. Chem. 1992, 57, 2768-2771).

Thereafter, Compound 9 may be obtained by converting Compound 22 into sulfonate in the presence of a base, and then subjecting the sulfonate to the epoxidation under basic conditions. Examples of the sulfonating agent used in conversion into sulfonate include p-toluenesulfonyl chloride, benzenesulfonyl chloride, 2,4,6-trimethoxybenzenesulfonyl chloride, 2,4,6-trimethylbenzenesulfonyl chloride, methanesulfonyl chloride, ethanesulfonyl chloride, benzylsulfonyl chloride, trifluoromethanesulfonyl chloride, p-toluenesulfonic anhydride, benzenesulfonic anhydride, 2,4,6-trimethoxybenzenesulfonic anhydride, 2,4,6-trimethylbenzenesulfonic anhydride, methanesulfonic anhydride, ethanesulfonic anhydride, benzylsulfonic anhydride, and trifluoromethanesulfonic anhydride. Examples of the base used therein include triethylamine, diisopropylethylamine, tri-n-butylamine, tri-n-propylamine, dicyclohexylmethylamine, N-methylmorpholine, 1,8-diazabicyclo[5.4.0]-7-undecene, pyridine, 2,6-lutidine, 2,4,6-collidine, dimethylaminopyridine, and imidazole. Examples of the solvent include toluene, xylene, heptane, hexane, pentane, dichloromethane, chlorobenzene, dichloroethane, chloroform, di-i-propyl ether, cyclopentyl methyl ether, t-butyl methyl ether, tetrahydrofuran, dimethoxyethane, dioxane, methyl acetate, and ethyl acetate. The reaction temperature is usually in the range of −50 to 100° C. Examples of the base used in the subsequent epoxidation include sodium methoxide, sodium ethoxide, sodium-n-propoxide, sodium-i-propoxide, sodium-n-butoxide, sodium-i-butoxide, sodium-s-butoxide, sodium-t-butoxide, potassium methoxide, potassium ethoxide, potassium-n-propoxide, potassium-i-propoxide, potassium-n-butoxide, potassium-i-butoxide, potassium-s-butoxide, potassium-t-butoxide, lithium methoxide, lithium ethoxide, lithium-n-propoxide, lithium-i-propoxide, lithium-n-butoxide, lithium-i-butoxide, lithium-s-butoxide, lithium-t-butoxide, potassium hydroxide, sodium hydroxide, lithium hydroxide, potassium carbonate, sodium carbonate, lithium carbonate, potassium phosphate, sodium phosphate, lithium phosphate, triethylamine, diisopropylethylamine, tri-n-butylamine, tri-n-propylamine, dicyclohexylmethylamine, N-methylmorpholine, 1,8-diazabicyclo[5.4.0]-7-undecene, pyridine, 2,6-lutidine, 2,4,6-collidine, dimethylaminopyridine, and imidazole. Examples of the solvent include methanol, ethanol, n-propanol, i-propanol, n-butanol, i-butanol, s-butanol, t-butanol, n-amyl alcohol, i-amyl alcohol, s-amyl alcohol, t-amyl alcohol, cyclohexanol, cyclopropanol, tetrahydrofuran, dimethoxyethane, dioxane, dimethylformamide, dimethylacetamide, dimethylimidazolidinone, dimethyl sulfoxide, and acetonitrile. The reaction temperature is usually in the range of −50 to 100° C. In a preferred embodiment, Compound 9 may be obtained by reacting Compound 22 with methanesulfonyl chloride at −10 to 10° C. in methylene chloride in the presence of triethylamine, and then reacting the obtained reaction mixture with sodium methoxide at −10 to 10° C. in methanol.

Scheme 5:

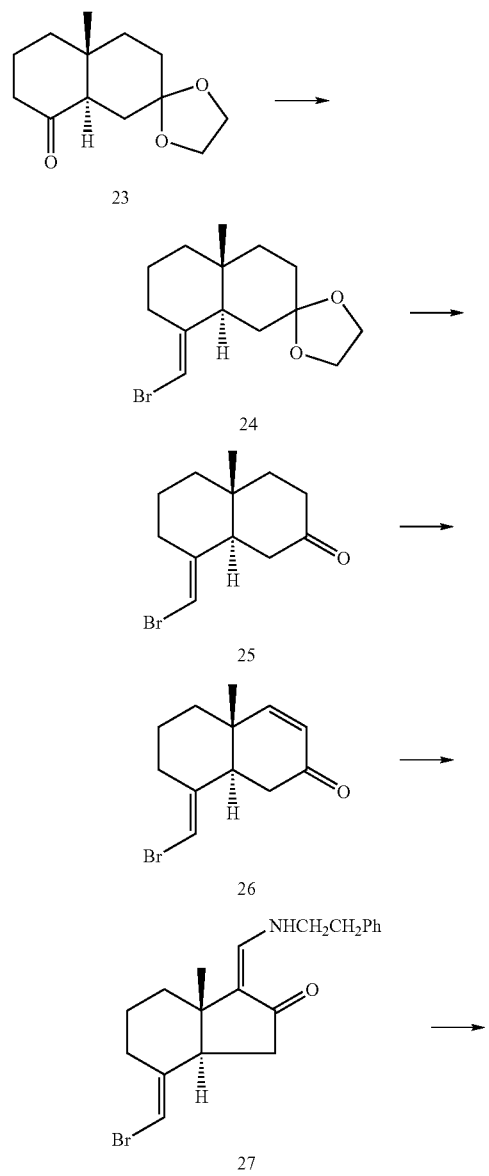

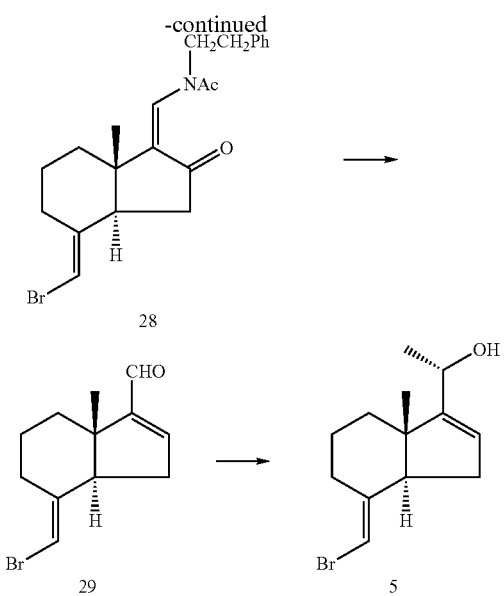

The starting material Compound 23 is a known material, and may be synthesized, for example, in accordance with the method described in J. Org. Chem. 1966, 31, 2933-2941. Compound 24 may be obtained by reacting Compound 23 with Phosphorus ylide, which has been synthesized from bromomethyltriphenylphosphonium bromide and a suitable base, and then subjecting the obtained compound to acid hydrolysis. Examples of the base used in the synthesis of phosphorus ylide include potassium hexamethyldisilazide, sodium hexamethyldisilazide, lithium hexamethyldisilazide, lithium diisopropylamide, lithium dicyclohexylamide, lithium amide, sodium amide, potassium amide, sodium hydride, potassium hydride, lithium hydride, potassium-t-butoxide, sodium-t-butoxide, lithium-t-butoxide, potassium-t-pentoxide, sodium-t-pentoxide, and lithium-t-pentoxide. Examples of the solvent include toluene, xylene, heptane, hexane, pentane, dichloromethane, chlorobenzene, dichloroethane, chloroform, di-i-propyl ether, cyclopentyl methyl ether, t-butyl methyl ether, tetrahydrofuran, dimethoxyethane, dioxane, and ethyl acetate. The reaction temperature is usually in the range of −50 to 100° C. In a preferred embodiment, Compound 24 may be obtained by allowing Compound 23 to react with phosphorus ylide, which has been prepared from potassium hexamethyldisilazide and bromomethyltriphenylphosphonium bromide at room temperature, at 0 to 40° C. in toluene.

Compound 25 may be obtained by subjecting the obtained Compound 24 to acid hydrolysis. Examples of the acid which may be used include formic acid, acetic acid, oxalic acid, maleic acid, fumaric acid, methanesulfonic acid, benzenesulfonic acid, p -toluenesulfonic acid, succinic acid, malonic acid, citric acid, gluconic acid, mandelic acid, benzoic acid, salicylic acid, trifluoroacetic acid, tartaric acid, propionic acid, glutaric acid, hydrochloric acid, hydrobromic acid, hydroiodic acid, sulfuric acid, and phosphoric acid. The reaction temperature is usually in the range of −50 to 150° C. In a preferred embodiment, Compound 25 may be obtained by adding acetic acid and water to Compound 24 and then carrying out the reaction at 60 to 100° C.

Thereafter, Compound 26 may be obtained by oxidization of Compound 25 with ortho-iodoxybenzoic acid. Examples of the solvent which may be used include dimethyl sulfoxide, dimethylformamide, dimethylacetamide, dimethylimidazolidinone, and N-methylpyrrolidinone. The reaction temperature is usually in the range of 0 to 150° C. In a preferred embodiment, Compound 26 may be obtained by reacting Compound 25 with ortho-iodoxybenzoic acid which has been synthesized according to the method described in J. Org. Chem. 1999, 64, 4537-4538, at 60 to 100° C. in dimethyl sulfoxide.

Compound 27 may be obtained by reacting the obtained Compound 26 with phenethyl azide in the presence of Lewis acid. Examples of the Lewis acid which may be used include trimethylsilyl trifluoromethanesulfonate, triethylsilyl trifluoromethanesulfonate, boron trifluoride etherate, boron trifluoride tetrahydrofuran complex, titanium tetrachloride, aluminum chloride, magnesium trifluoromethanesulfonate, copper trifluoromethanesulfonate, silver trifluoromethanesulfonate, titanium trifluoromethanesulfonate, aluminum trifluoromethanesulfonate, yttrium trifluoromethanesulfonate, scandium trifluoromethanesulfonate, lanthanum trifluoromethanesulfonate, samarium trifluoromethanesulfonate, and cerium trifluoromethanesulfonate. Examples of the solvent include toluene, xylene, heptane, hexane, pentane, dichloromethane, chlorobenzene, dichloroethane, chloroform, di-i-propyl ether, cyclopentyl methyl ether, t-butyl methyl ether, tetrahydrofuran, dimethoxyethane, dioxane, methyl acetate, and ethyl acetate. The reaction temperature is usually in the range of −50 to 100° C. In a preferred embodiment, Compound 27 may be obtained by reacting Compound 26 with phenethyl azide, which has been synthesized according to the method described in Org. Lett. 2001, 3, 4091-4094, at −20 to 20° C. in dichloromethane in the presence of trimethylsilyl trifluoromethanesulfonate.

Thereafter, Compound 28 may be obtained by reacting Compound 27 with acetyl chloride in the presence of a base. Examples of the base which may be used include triethylamine, diisopropylethylamine, tri-n-butylamine, tri-n-propylamine, dicyclohexylmethylamine, N-methylmorpholine, 1,8-diazabicyclo[5.4.0]-7-undecene, pyridine, 2,6-lutidine, 2,4,6-collidine, dimethylaminopyridine, imidazole, potassium hydroxide, sodium hydroxide, lithium hydroxide, potassium carbonate, sodium carbonate, lithium carbonate, potassium phosphate, sodium phosphate, and lithium phosphate. Examples of the solvent include toluene, xylene, heptane, hexane, pentane, dichloromethane, chlorobenzene, dichloroethane, chloroform, di-i-propyl ether, cyclopentyl methyl ether, t-butyl methyl ether, tetrahydrofuran, dimethoxyethane, dioxane, methyl acetate and ethyl acetate, however, the solvent is not necessarily used. The reaction temperature is usually in the range of −50 to 100° C. In a preferred embodiment, Compound 28 may be obtained by reacting Compound 27 with acetyl chloride at room temperature in pyridine.

Compound 29 may be obtained by reduction of the obtained Compound 28 with a reducing agent, followed by acid hydrolysis. Examples of the reducing agent which may be used include lithium aluminum hydride, lithium trimethoxyalminium hydride, lithium tri-t-butoxyaluminum hydride, sodium aluminum hydride, sodium triethoxyalminium hydride, sodium bis(methoxyethoxy)aluminum hydride, sodium borohydride, sodium boron cyanhydride, sodium trimethoxyborohydride, lithium borohydride, lithium boron cyanhydride, lithium triethylborohydride, lithium tri-s-butylborohydride, lithium tri-t-butylborohydride, calcium borohydride, potassium borohydride, potassium triisopropoxyborohydride, potassium tri-s-butylborohydride, and tetramethylammonium borohydride. Examples of the solvent include methanol, ethanol, n-propanol, i-propanol, ethylene glycol, tetrahydrofuran, t-butyl methyl ether, diethyl ether, and dimethoxy ethane. The reaction temperature is usually in the range of −50 to 100° C. Examples of the acid which may be used in the subsequent acid hydrolysis include hydrochloric acid, hydrobromic acid, hydroiodic acid, sulfuric acid, phosphoric acid, formic acid, acetic acid, oxalic acid, maleic acid, fumaric acid, methanesulfonic acid, benzenesulfonic acid, p-toluenesulfonic acid, succinic acid, malonic acid, citric acid, gluconic acid, mandelic acid, benzoic acid, salicylic acid, trifluoroacetic acid, tartaric acid, propionic acid, and glutaric acid. Examples of the solvent include tetrahydrofuran, dioxane, dimethoxyethane, methanol, ethanol, dimethylformamide, dimethylacetamide, and dimethyl sulfoxide. The reaction temperature is usually in the range of 0 to 150° C. In a preferred embodiment, Compound 29 may be obtained by reacting Compound 28 with sodium borohydride at −20 to 20° C. in methanol, and then adding 1-5 N sulfuric acid to the mixture to allow the hydrolysis reaction at 50 to 90° C. in tetrahydrofuran.

Compound 5 may be obtained by methylating Compound 29 using dimethylzinc and a catalytic amount of (1R)-trans-N,N'-1,2-cyclohexanediylbis(1,1,1-trifluoromethanesulfonamide) and tetraisopropoxy titanium. The catalyst may be used in the range of 0.001 to 0.5 equivalents with respect to Compound 29. Examples of the solvent include toluene, xylene, heptane, hexane, pentane, dichloromethane, chlorobenzene, dichloroethane, chloroform, di-i-propyl ether, cyclopentyl methyl ether, t-butyl methyl ether, tetrahydrofuran, dimethoxyethane, dioxane, and ethyl acetate. The reaction temperature is usually in the range of −50 to 100° C. In a preferred embodiment, Compound 5, which is the compound of Formula (5), may be obtained by adding Compound 29 to the mixture prepared from (1R)-trans-N,N'-1,2-cyclohexanediylbis(1,1,1-trifluoromethanesulfonamide), tetraisopropoxy titanium and dimethylzinc, and allowing the resulting mixture to react at room temperature in the solvent such as t-butyl methyl ether.

EXAMPLES

An embodiment of the present invention will now be described in more detail with reference to the following examples. In the following examples, NMR (nuclear magnetic resonance spectrum; tetramethylsilane or residual proton in deuterated chloroform was used as an internal standard) was measured using JEOL JNM-EX-270 (270 MHz), Varian mercury 300 (300 MHz) or JEOL JNM-ECP400 (400 MHz). For thin layer chromatography, TLC plates Silica gel 60 F254 produced by Merck was used.

Example 1

Synthesis of (1R,3aR,4S,7aS,3'S)-3',7a-dimethyl-4-hydroxyoctahydrospiro(indene-1,2'-oxirane) (Compound 7)

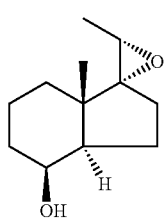

(Z,3aR,4S,7aS)-1-ethylidene-octahydro-7a-methyl-1H-indene-4-ol (Compound 6: 663.1 mg, 3.18 mmol) synthesized in accordance with the method described in J. Org. Chem. 2001, 66, 626-628 was dissolved in ethyl acetate (3.1 ml), and the solution was cooled to 4.4° C. Meta-chloroperbenzoic acid (913 mg, 3.44 mmol) was added to the reaction solution over 9 minutes. After stirring the reaction solution at 2° C. for 1 hour, aqueous sodium hydrogen carbonate solution (2 ml) and aqueous sodium sulfite solution (1 ml) were added thereto, and the mixed solution was stirred and separated. The obtained organic layer was washed with aqueous sodium hydrogen carbonate solution (2 ml) and dried over magnesium sulfate, and then the solvent was evaporated under reduced pressure. To the obtained reaction mixture, seed crystals were added, and heptane (1.8 ml) was added thereto, followed by collecting the precipitated crystals by filtration to obtain (1R,3aR,4S,7aS,3'S)-3',7a-dimethyl-4-hydroxyoctahydrospiro(indene-1,2'-oxirane) (382.8 mg, 61%).

$^1$H NMR (CDCl$_3$) δ: 1.13 (3H, s), 1.36 (3H, d, J=5.8 Hz), 1.40-1.90 (10 H, m), 2.20-2.32 (1H, m), 2.97 (1H, q, J=5.8 Hz), 4.15-4.17 (1H, m)

Rf value (silica gel plate, developing solvent; hexane:ethyl acetate=2:1): 0.4

Example 2

Synthesis of (1R,3aR,7aS,3'S)-3',7a-dimethyl-4-oxooctahydrospiro(4H-indene-1,2'-oxirane) (Compound 8)

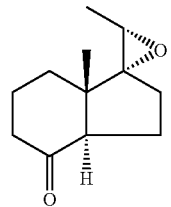

(1R,3aR,4S,7aS,3'S)-3',7a-dimethyl-4-hydroxyoctahydrospiro(indene-1,2'-oxirane) (Compound 7: 4.66 g, 23.74 mmol) and N-methylmorpholine-N-oxide (4.17 g, 35.61 mmol) were dissolved in acetonitrile (18.5 ml). After cooling the solution to 20° C., a solution of tetra-n-propylammonium perruthenate (167 mg) in acetonitrile (2 ml) was added dropwise thereto over 10 minutes. After stirring the reaction solution at room temperature for 1 hour, the solvent was evaporated. Saturated brine (7.6 ml) and water (1.9 ml) were added to the reaction mixture, and heptane (70 ml) was added thereto, followed by separating the solution. The obtained organic layer was washed by adding saturated brine (7.6 ml) and water (1.9 ml), and dried over sodium sulfate. The solvent was evaporated under reduced pressure to obtain (1R,3aR,7aS,3'S)-3',7a-dimethyl-4-oxooctahydrospiro(4H-indene-1,2'-oxirane) (4.65 g, quantitatively).

$^1$H NMR (CDCl$_3$) δ: 0.86 (3H, s), 1.41 (3H, d, J=5.8 Hz), 1.45-1.65 (2H, m), 1.70-2.10 (5H, m), 2.22-2.35 (3H, m), 2.87 (1H, dd, J=11.5 Hz, 7.4 Hz), 3.04 (1H, q, J=5.8 Hz)

Rf value (silica gel plate, developing solvent; hexane:ethyl acetate=2:1): 0.5

Example 3

Synthesis of (E)-(1R,3aR,7aS,3'S)-3',7a-dimethyl-4-(bromomethylene)octahydrospiro(4H-indene-1,2'-oxirane) (Compound 9)

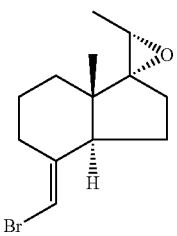

Bromomethyltriphenylphosphonium bromide (13.67 g, 31.14 mmol) was suspended in toluene (23 ml), and potassium t-pentoxide (1.7 M in toluene, 18.2 ml, 30.86 mmol) was added dropwise thereto at −10° C. over 15 minutes. The obtained solution was stirred at 0° C. for 30 minutes and then cooled to −15° C., and a solution of (1R,3aR,7aS,3'S)-3',7a-dimethyl-4-oxooctahydrospiro(4H-indene-1,2'-oxirane) (Compound 8: 4.65 g, 23.9 mmol) in toluene (3 ml) was added dropwise thereto over 13 minutes. After stirring the reaction solution at −15° C. for 1 hour, saturated aqueous ammonium chloride solution (5 ml) and hexane (50 ml) were added thereto. The organic layer was separated and the precipitates were removed by filtration, followed by evaporation of the solvent. Hexane (50 ml) was added to the obtained reaction mixture, and the precipitates were removed by filtration, followed by evaporation of the solvent. Ethanol (20 ml) was added to the obtained reaction mixture, and the resulting mixture was heated to dissolve at 40° C. Water (4 ml) was added thereto, and the resulting mixture was cooled to 0° C., followed by stirring it for 1 hour. The precipitated crystals were collected by filtration and dried to obtain (E)-(1R,3aR,7aS,3'S)-3',7a-dimethyl-4-(bromomethylene)octahydrospiro(4H-indene-1,2'-oxirane) (3.9 g, 60.6%).

$^1$H NMR (CDCl$_3$) δ: 0.79 (3H, s), 1.38 (3H, d, J=5.8 Hz), 1.40-1.85 (8H, m), 2.18-2.33 (1H, m), 2.36-2.50 (1H, m), 2.80-2.93 (1H, m), 2.99 (1H, q, J=5.8 Hz), 5.72 (1H, dd, J=1.7 Hz, 1.7 Hz)

Rf value (silica gel plate, developing solvent; hexane:ethyl acetate=5:1): 0.6

Example 4

Synthesis of (S)-1-{(3aS,7E,7aR)-7-(bromomethylene)-3a,4,5,6,7,7a-hexahydro-3a-methyl-1H-indene-3-yl}ethanol (Compound 5)

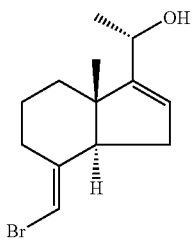

(E)-(1R,3aR,7aS,3'S)-3',7a-dimethyl-4-(bromomethylene)octahydrospiro(4H-indene-1,2'-oxirane) (Compound 9: 4.65 g, 17.15 mmol) and aluminum triisopropoxide (350 mg, 1.715 mmol) were weighed, and toluene (20 ml) was added thereto, followed by stirring the resulting mixture at 130° C. for 1 hour and 15 minutes. After cooling the reaction solution to room temperature, aqueous sulfuric acid solution (0.5 M, 14 ml) and heptane (90 ml) were added thereto, and the resulting solution was separated. The obtained organic layer was sequentially washed with saturated aqueous sodium hydrogen carbonate solution (10 ml) and brine (10 ml), and dried over sodium sulfate. The solvent was evaporated to obtain a white solid of (S)-1-{(3aS,7E,7aR)-7-(bromomethylene)-3a,4,5,6,7,7a-hexahydro-3a-methyl-1H-indene-3-yl}ethanol (4.63 g, 99.6%).

$^1$H NMR (CDCl$_3$) δ: 0.82 (3H, s), 1.35 (3H, d, J=6.6 Hz), 1.40-1.62 (2H, m), 1.68-1.90 (4H, m), 2.05-2.45 (3H, m), 2.80-2.97 (1H, m), 4.37 (1H, q, J=6.6 Hz), 5.62-5.67 (1H, m), 5.76-5.80 (1H, m)

Rf value (silica gel plate, developing solvent; hexane:ethyl acetate=5:1): 0.2

Example 5

Synthesis of 2-bromo-N-(2,2,3,3,3-pentafluoropropyl)acetamide 2,2,3,3,3-Pentafluoropropylamine (produced by Synquest) (389 g) was dissolved in ethyl acetate (1.56 l), and N,N-dimethylaniline (316 g) was added thereto. The resulting mixture was cooled to −10° C., and bromoacetyl bromide (500 g) was added dropwise thereto, followed by stirring the resulting mixture at a temperature between 10° C. and 0° C. for 2 hours. After completion of the reaction, the organic layer was sequentially washed with hydrochloric acid, aqueous sodium bicarbonate and with brine, and dried over magnesium sulfate, followed by evaporation under reduced pressure to obtain 678 g of 2-bromo-N-(2,2,3,3,3-pentafluoropropyl)acetamide as white powder.

$^1$H NMR (CDCl$_3$) δ: 3.95 (s, 2H), 3.93-4.09 (m, 2H), 6.74 (bs, 1H)

Example 6

Synthesis of 2-[(S)-1-{(3aS,7E,7aR)-7-(bromomethylene)-3a,4,5,6,7,7a-hexahydro-3a-methyl-1H-indene-3-yl}ethoxy]-N-(2,2,3,3,3-pentafluoropropyl)acetamide (Compound 2)

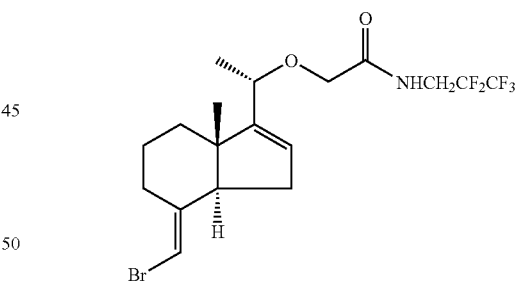

Under a nitrogen atmosphere, a solution of sodium hexamethyldisilazide in tetrahydrofuran (1.1 M, 5.31 ml, 5.84 mmol) was cooled to −15° C., and a solution of (S)-1-{(3aS,7E,7aR)-7-(bromomethylene)-3a,4,5,6,7,7a-hexahydro-3a-methyl-1H-indene-3-yl}ethanol (Compound 5: 633.7 mg, 2.337 mmol) in dimethylformamide (1 ml) was added thereto over 4 minutes. The resulting mixture was stirred at −15° C. for 7 minutes, and a solution of 2-bromo-N-(2,2,3,3,3-pentafluoropropyl)acetamide (726 mg, 2.688 mmol) in dimethylformamide (1 ml) was added thereto over 5 minutes. After stirring the reaction solution at −5° C. for 30 minutes, aqueous ammonium chloride solution (5 ml) and hexane (20 ml) were added thereto, and the separation of the solution was conducted. The obtained organic layer was sequentially washed with water (5 ml) and saturated brine (4 ml)/water (1 ml), and the solvent was evaporated. The obtained crude product was purified by silica gel column chromatography to obtain 2-[(S)-1-{(3aS,7E,7aR)-7-(bromomethylene)-3a,4,5,6,7,7a-hexahydro-3a-methyl-1H-indene-3-yl}ethoxy]-N-(2,2,3,3,3-pentafluoropropyl)acetamide (1.08 g, quantitatively).

$^1$H NMR (CDCl$_3$) δ: 0.81 (3H, s), 1.37 (3H, d, J=6.3 Hz), 1.42-1.58 (1H, m), 1.67-1.87 (4H, m), 2.08-2.32 (2H, m), 2.35-2.46 (1H, m), 2.85-2.95 (1H, m), 3.87 (1H, d, J=15.6 Hz), 4.01 (1H, d, J=15.6 Hz), 3.92-4.10 (3H, m), 5.60-5.62 (1H, m), 5.74-5.81 (1H, m), 6.80-7.0 (1H, m)

Rf value (silica gel plate, developing solvent; hexane:ethyl acetate:methylene chloride=10:1:10): 0.4

Example 7

Synthesis of 1-{(E,3S,3aS,7aR)-7-(bromomethylene)-octahydro-3a-methyl-1H-indene-3-yl}ethanone (Compound 11)

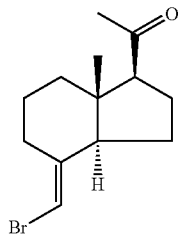

(S)-2-{(E,3R,3aR,7aR)-7-(bromomethylene)-octahydro-3a-methyl-1H-indene-3-yl}propanal (Compound 10: 43 mg, 0.151 mmol) synthesized according to the method described in Org. Lett. 2003, 5, 4859-4862 was dissolved in dimethylformamide (300 μl), and copper (II) acetate (3.1 mg, 0.0171 mmol), bipyridyl (2.8 mg, 0.0179 mmol) and triethylenediamine (17.4 mg, 0.155 mmol) were added thereto. The resulting mixture was heated to 80° C. and stirred for 4 hours with streaming oxygen. After cooling the mixture to room temperature, 2N hydrochloric acid was added thereto, and the resulting mixture was extracted with diethyl ether. The organic layer was washed with water and saturated brine, dried over sodium sulfate, and evaporated. The obtained product was purified by flash column chromatography to obtain 1-{(E,3S,3aS,7aR)-7-(bromomethylene)-octahydro-3a-methyl-1H-indene-3-yl}ethanone (24.1 mg, 58.8%).

$^1$HNMR (CDCl$_3$) δ: 5.70 (t, J=1.8 Hz, 1H), 2.80-2.95 (m, 1H), 2.67 (t, J=9.0 Hz, 1H), 2.00-2.30 (m, 3H), 2.12 (s, 3H), 1.45-1.85 (m, 7H), 0.50 (s, 3H)

Rf value (silica gel plate, developing solvent; hexane:ethyl acetate=6:1): 0.4

Example 8

Synthesis of 1-{(E,1R,3aS,7aS)-1-bromo-4-(bromomethylene)-octahydro-7a-methyl-1H-indene-1-yl}ethanone (Compound 12)

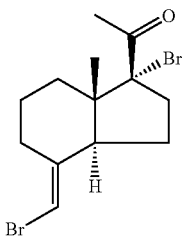

1-{(E,3S,3aS,7aR)-7-(bromomethylene)-octahydro-3a-methyl-1H-indene-3-yl}ethanone (Compound 11: 100 mg, 0.369 mmol) was dissolved in methylene chloride (400 μl), and hexamethyldisilazane (160 μl, 0.758 mmol) and iodotrimethylsilane (80 μl, 0.562 mmol) were added thereto at −20° C., followed by stirring the resulting mixture for 10 minutes. The mixture was warmed to room temperature and stirred for another 100 minutes. The solvent was removed by evaporator, and the residue was dissolved in hexane. Saturated aqueous sodium hydrogen carbonate was added to the reaction solution and the resulting mixture was extracted with hexane. The combined organic layer was washed with saturated brine, dried over sodium sulfate, and evaporated to obtain a crude product of silylenol ether (143 mg). The obtained crude product was dissolved in tetrahydrofuran (700 μl), and a solution of triethylamine (50 μl, 0.359 mmol) and tetra-n-butylammonium tribromide (179 mg, 0.371 mmol) in tetrahydrofuran (400 μl) was added thereto at 0° C. After stirring the resulting mixture for 15 minutes, the mixture was warmed to room temperature and stirred for another 1 hour. The reaction solution was diluted with diethyl ether, and saturated aqueous sodium hydrogen carbonate was added thereto. The aqueous layer was extracted with diethyl ether. The combined organic layer was washed with aqueous sodium thiosulfate solution, aqueous potassium hydrogen sulfate solution and with saturated brine, and dried over sodium sulfate, followed by evaporation to obtain a crude product. The product was purified by flash column chromatography to obtain 1-{(E,1R,3aS,7aS)-1-bromo-4-(bromomethylene)-octahydro-7a-methyl-1H-indene-1-yl}ethanone as a white solid (99.2 mg, 76.9%).

$^1$H NMR (CDCl$_3$) δ: 5.74 (t, J=1.8 Hz, 1H), 3.08 (ddd, J=15.9 Hz, 12.0 Hz, 3.9 Hz, 1H), 2.80-3.00 (m, 2H), 2.40 (s, 3H), 2.38 (ddd, J=16.2 Hz, 9.6 Hz, 6.0 Hz, 1H), 2.05 (ddd, J=12.9 Hz, 12.9 Hz, 3.9 Hz, 1H), 1.40-2.00 (m, 6H), 0.67 (s, 3H)

Rf value (silica gel plate, developing solvent; hexane:ethyl acetate=6:1): 0.5

Example 9

Synthesis of 1-{(3aS,7E,7aR)-7-(bromomethylene)-3a,4,5,6,7,7a-hexahydro-3a-methyl-1H-indene-3-yl}ethanone (Compound 13)

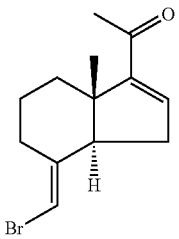

1-{(E,1R,3aS,7aS)-1-bromo-4-(bromomethylene)-octahydro-7a-methyl-1H-indene-1-yl}ethanone (Compound 12: 100 mg, 0.369 mmol) was dissolved in dimethylformamide (1.6 ml), and lithium bromide (35.8 mg, 0.412 mmol) and lithium carbonate (27.4 mg, 0.371 mmol) were added thereto. The resulting mixture was heated to 100° C. and stirred for 3 hours. After cooling the reaction solution to room temperature, water was added thereto, and the resulting mixture was extracted with diethyl ether. The organic layer was washed with saturated brine, dried over sodium sulfate, and evaporated to obtain a crude product. The product was purified by flash column chromatography to obtain 1-{(3aS,7E,7aR)-7-(bromomethylene)-3a,4,5,6,7,7a-hexahydro-3a-methyl-1H-indene-3-yl}ethanone (71.6 mg, 94.0%) as a white solid.

¹H NMR (CDCl₃) δ: 6.68 (dd, J=3.0 Hz, 2.1 Hz, 1H), 5.75 (s, 1H), 2.75-2.90 (m, 1H), 2.25-2.50 (m, 4H), 2.27 (s, 3H), 1.65-1.85 (m, 3H), 1.35-1.50 (m, 1H), 0.81 (s, 3H)

Rf value (silica gel plate, developing solvent; hexane:ethyl acetate=6:1): 0.4

Example 10

Synthesis of (S)-1-{(3aS,7E,7aR)-7-(bromomethylene)-3a,4,5,6,7,7a-hexahydro-3a-methyl-1H-indene-3-yl}ethanol (Compound 5) (part 2)

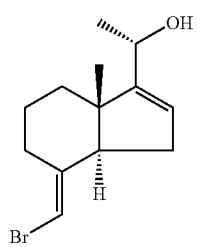

1-{(3aS,7E,7aR)-7-(bromomethylene)-3a,4,5,6,7,7a-hexahydro-3a-methyl-1H-indene-3-yl}ethanone (Compound 13: 24.7 mg, 0.0918 mmol) was dissolved in toluene (200 μl), and (R)-2-methyl-CBS-oxazaborolidine (18 μl, 0.018 mmol, 1.0 M in toluene) and borane dimethyl sulfide (26 μl, 0.274 mmol) were added thereto at −20° C., followed by stirring the resulting mixture for 1 hour. Methanol (100 μl) was added to the reaction solution, and when generation of hydrogen gas stopped, diethyl ether and water were added thereto. After separating the organic layer, the aqueous layer was extracted with diethyl ether. The combined organic layer was washed with saturated brine, dried over sodium sulfate, and evaporated. The obtained crude product was purified by flash column chromatography to obtain (S)-1-{(3aS,7E,7aR)-7-(bromomethylene)-3a,4,5,6,7,7a-hexahydro-3a-methyl-1H-indene-3-yl}ethanol (23.6 mg, 94.8%) as a white solid. The spectrum data thereof agreed with the data described in Example 4.

Example 11

Synthesis of (S)-2-{(3R,3aR,7S,7aR)-octahydro-7-hydroxy-3a-methyl-1H-indene-3-yl}propanal (Compound 15)

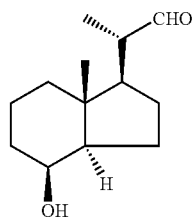

Under a nitrogen atmosphere, a solution of (1R,3aR,4S,7aR)-octahydro-1-{(S)-1-hydroxypropane-2-yl}-7a-methyl-1H-indene-4-ol (Compound 14: 2.05 g, 9.659 mmol) synthesized according to the method described in J. Org. Chem. 1986, 51, 1264-1269, 4-acetamide-2,2,6,6-tetramethyl-1-piperidinyloxy free radical (155 mg, 0.7244 mmol) and tetra-n-butylammonium chloride (134 mg, 0.4830 mmol) in methylene chloride (90 ml) was cooled in an ice bath, and 0.5 M sodium hydrogen carbonate (45 ml) and 0.05 M potassium carbonate (45 ml) were added thereto. N-chlorosuccinimide (3.87 g, 28.98 mmol) was added thereto over 10 minutes. The reaction solution was stirred in the ice bath for 1.5 hours, at 10° C. to 18° C. for 4.5 hours, at 5° C. for 11.5 hours, and then at 10° C. to 15° C. for 4.25 hours. After adding saturated aqueous sodium thiosulfate solution (15 ml), the resulting mixture was stirred at 15° C. for 20 minutes. The resulting mixture was extracted 3 times with methylene chloride. The combined organic layer was dried over sodium sulfate, and evaporated under reduced pressure. The crude product (2.90 g) was purified by flash column chromatography to obtain (S)-2-{(3R,3aR,7S,7aR)-octahydro-7-hydroxy-3a-methyl-1H-indene-3-yl}propanal (1.87 g).

The spectrum data thereof agreed with that of described in the literature (Eur. J. Org. Chem. 1999, 9, 2241-2248).

Example 12

Synthesis of (S)-1-{(3S,3aS,7S,7aR)-octahydro-7-hydroxy-3a-methyl-1H-indene-3-yl}ethyl formate (Compound 16)

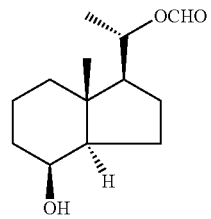

Under a nitrogen atmosphere, a solution of (S)-2-{(3R,3aR,7S,7aR)-octahydro-7-hydroxy-3a-methyl-1H-indene-3-yl}propanal (Compound 15: 1.85 g, 8.797 mmol) in methylene chloride (30 ml) was cooled in an ice bath, and sodium dihydrogen phosphate dihydrate (6.86 g, 43.99 mmol) was added thereto. Meta-chloroperbenzoic acid (3.50 g, 13.2 mmol, calculated as 65%) was added thereto over 10 minutes. The reaction solution was stirred in the ice bath for 30 minutes, and at 17° C. to 21° C. for 12.5 hours. The reaction mixture was transferred to a separatory funnel such that insoluble matters were not included therein (the reaction vessel was washed with ethyl acetate), and water (40 ml) and ethyl acetate were added thereto. The aqueous layer was extracted twice with ethyl acetate. The combined organic layer was washed with saturated aqueous sodium thiosulfate solution (45 ml), saturated aqueous sodium hydrogen carbonate solution (25 ml) and with saturated brine (50 ml), and dried over sodium sulfate, followed by evaporation under reduced pressure. The crude product (2.41 g) was purified by flash column chromatography to obtain (S)-1-{(3S,3aS,7S,7aR)-octahydro-7-hydroxy-3a-methyl-1H-indene-3-yl}ethyl formate (1.80 g).

¹H NMR (CDCl₃) δ: 8.02 (1H, s), 4.90-5.20 (1H, m), 4.00-4.20 (1H, m), 1.10-2.00 (13H, m), 1.27 (3H, d, J=6.1 Hz), 0.97 (3H, s)

Rf value (silica gel plate, developing solvent; hexane:methylene chloride:diethyl ether=1:1:1): 0.4

Example 13

Synthesis of (S)-1-{(3S,3aR,7aR)-octahydro-3a-methyl-7-oxo-1H-indene-3-yl}ethyl formate (Compound 17)

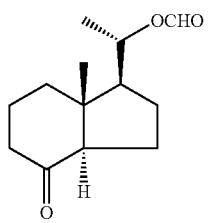

Under a nitrogen atmosphere, a solution of (S)-1-{(3S,3aS, 7S,7aR)-octahydro-7-hydroxy-3a-methyl-1H-indene-3-yl}ethyl formate (Compound 16: 899.6 mg, 3.975 mmol) in acetonitrile (10 ml) was cooled in an ice bath, and tetra-n-propylammonium perruthenate (35 mg, 0.0994 mmol) was added thereto. The reaction mixture was stirred in the ice bath for 3 minutes, and at room temperature (23° C.) for 45 minutes. The reaction mixture was filtered through Celite, and the resulting mixture was washed with ethyl acetate, followed by evaporation under reduced pressure. The crude product was purified by flash column chromatography to obtain (S)-1-{(3S,3aR,7aR)-octahydro-3a-methyl-7-oxo-1H-indene-3-yl}ethyl formate (865.1 mg).

$^1$H NMR (CDCl$_3$) δ: 8.02 (1H, s), 5.08 (1H, q, J=6.3 Hz), 2.48 (1H, dd, J=11.2, 6.8 Hz), 2.10-2.40 (2H, m), 1.45-2.10 (9H, m), 1.31 (3H, d, J=6.3 Hz), 0.66 (3H, s)

Rf value (silica gel plate, developing solvent; hexane:methylene chloride:diethyl ether=1:1:1): 0.6

Example 14

Synthesis of (S)-1-{(E,3S,3aS,7aR)-7-(bromomethylene)-octahydro-3a-methyl-1H-indene-3-yl}ethanol (Compound 18)

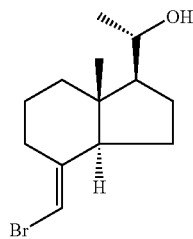

Under a nitrogen atmosphere, a suspension of bromomethyltriphenylphosphonium bromide (319 mg, 0.7304 mmol) in toluene (0.4 ml) was cooled in an ice bath, and potassium hexamethyldisilazide (0.5 M in toluene, 1.3 ml, 0.6492 mmol) was added dropwise thereto. The reaction mixture was stirred at 0° C. for 1 hour and 20 minutes, and at room temperature for 8 minutes, and then heated to 42° C. A solution of (S)-1-{(3S,3aR,7aR)-octahydro-3a-methyl-7-oxo-1H-indene-3-yl}ethyl formate (Compound 17: 36.4 mg, 0.1623 mmol) in toluene (0.25 ml) was added thereto. The vessel of (S)-1-{(3S,3aR,7aR)-octahydro-3a-methyl-7-oxo-1H-indene-3-yl}ethyl formate (Compound 17) was washed with toluene (0.1 ml×2) and the washings were added. The reaction mixture was stirred at from 41° C. to 46° C., and then cooled in an ice bath. Saturated aqueous ammonium chloride solution (2 ml), water (5 ml) and methanol (1.5 ml) were added thereto, and the resulting mixture was extracted with hexane (25 ml). The organic layer was washed with saturated brine (5 ml), dried over sodium sulfate, and evaporated under reduced pressure. The obtained crude product (169.4 mg) was dissolved in dioxane (0.5 ml), and the resulting mixture was cooled in an ice bath. To the mixture, 50 v/v % sulfuric acid (0.5 ml) was added, and the reaction mixture was stirred at room temperature (22° C.) for 1.5 hours. After cooling the resulting mixture in an ice bath, the mixture was diluted with ether (10 ml). Potassium carbonate (0.56 g) and water (5 ml) were added thereto. After separating the organic layer, the aqueous layer was extracted twice with ether (10 ml). The combined organic layer was washed with saturated brine (5 ml), dried over sodium sulfate, and evaporated under reduced pressure. The obtained crude product was purified by flash column chromatography to obtain (S)-1-{(E,3S,3aS,7aR)-7-(bromomethylene)-octahydro-3a-methyl-1H-indene-3-yl}ethanol (20.6 mg, 46.5%).

$^1$H NMR (CDCl$_3$) δ: 5.67 (1H, bs), 3.72 (1H, q, J=6.3 Hz), 2.90-3.00 (1H, m), 1.80-2.10 (3H, m), 1.40-1.80 (7H, m), 1.20-1.40 (2H, m), 1.24 (3H, d, J=6.3 Hz), 0.57 (3H, s)

Rf value (silica gel plate, developing solvent; hexane:ethyl acetate=4:1): 0.2

Example 15

Synthesis of 1-{(E,3S,3aS,7aR)-7-(bromomethylene)-octahydro-3a-methyl-1H-indene-3-yl}ethanone (Compound 11) (part 2)

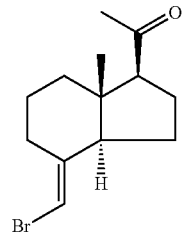

Under a nitrogen atmosphere, a solution of (S)-1-{(E,3S,3aS,7aR)-7-(bromomethylene)-octahydro-3a-methyl-1H-indene-3-yl}ethanol (Compound 18: 58.1 mg, 0.2127 mmol) and N-methylmorpholine-N-oxide (37.4 mg, 0.3190 mmol) in acetonitrile (2 ml) was cooled in an ice bath, and tetra-n-propylammonium perruthenate (3.7 mg, 0.01064 mmol) was added thereto. The reaction mixture was stirred at the same temperature for 5 minutes, and at room temperature (22° C.) for 50 minutes, and the resulting mixture was diluted with ethyl acetate. The mixture was filtered through Celite, and the solids were washed with ethyl acetate, followed by evaporation of the filtrate under reduced pressure. The obtained crude product was purified by flash column chromatography to obtain 1-{(E,3S,3aS,7aR)-7-(bromomethylene)-octahydro-3a-methyl-1H-indene-3-yl}ethanone (58.2 mg, 100%). The spectrum data thereof agreed with the data described in Example 7.

Example 16

Synthesis of (R)-1-{(E,3S,3aS,7aR)-7-(bromomethylene)-octahydro-3a-methyl-1H-indene-3-yl}ethanol (Compound 19)

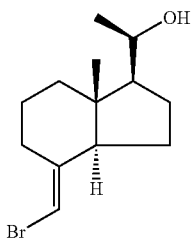

Under a nitrogen atmosphere, a solution of 1-{(E,3S,3aS,7aR)-7-(bromomethylene)-octahydro-3a-methyl-1H-indene-3-yl}ethanone (Compound 11: 302.7 mg, 1.116 mmol) in tetrahydrofuran (10 ml) was cooled to −20° C., and lithium tri-sec-butylborohydride (1.02 M in tetrahydrofuran, 1.64 ml, 1.674 mmol) was added dropwise thereto over 15 minutes. After stirring the reaction mixture at the same temperature for 1 hour, methanol (0.75 ml), 3 M aqueous sodium hydroxide solution (1.75 ml) and hydrogen peroxide solution (34.5%, 1.55 ml) were added thereto, and the resulting mixture was stirred in the ice bath for 30 minutes. The resulting mixture was extracted twice with ethyl acetate. The organic layer was washed with saturated brine (15 ml), dried over sodium sulfate, and evaporated under reduced pressure. The obtained crude product was purified by flash column chromatography to obtain (R)-1-{(E,3S,3aS,7aR)-7-(bromomethylene)-octahydro-3a-methyl-1H-indene-3-yl}ethanol (291.1 mg, 95.4%).

$^1$H NMR (CDCl$_3$) δ: 5.64 (1H, bs), 3.60-3.80 (1H, m), 2.80-3.00 (1H, m), 1.90-2.20 (2H, m), 1.00-1.90 (9H, m), 1.16 (3H, d, J=6.1 Hz), 1.12 (1H, d, J=5.8 Hz), 0.65 (3H, s)

Rf value (silica gel plate, developing solvent; hexane:ethyl acetate=3:1): 0.4

Example 17

Synthesis of (1Z,3aR,4E,7aS)-4-(bromomethylene)-1-ethylidene-octahydro-7a-methyl-1H-indene (Compound 20)

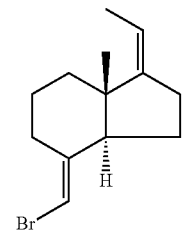

Under a nitrogen atmosphere, a solution of (R)-1-{(E,3S,3aS,7aR)-7-(bromomethylene)-octahydro-3a-methyl-1H-indene-3-yl}ethanol (Compound 19: 20.8 mg, 0.07613 mmol) and triphenylphosphine (50 mg, 0.1903 mmol) in tetrahydrofuran (0.35 ml) was cooled in an ice bath, and azodicarboxylic acid dimethyl ester (2.7 M in toluene, 73.3 μl, 0.1979 mmol) was added dropwise thereto. The reaction mixture was stirred at the same temperature for 5 minutes and at room temperature for 40 hours, and then evaporated under reduced pressure. The obtained crude product was purified by flash column chromatography to obtain (1Z,3aR,4E,7aS)-4-(bromomethylene)-1-ethylidene-octahydro-7a-methyl-1H-indene (13.4 mg, 69.1%).

$^1$H NMR (CDCl$_3$) δ: 5.68 (1H, bs), 5.20 (1H, qt, J=7.1, 2.0 Hz), 2.75-3.00 (1H, m), 2.05-2.50 (4H, m), 1.50-1.85 (6H, m), 1.67 (3H, dt, J=7.1, 2.0 Hz), 0.79 (3H, s)

Rf value (silica gel plate, developing solvent; hexane:ethyl acetate=4:1): 0.9

Example 18

Synthesis of (E,1R,3aR,7aS,3'S)-3',7a-dimethyl-4-(bromomethylene)octahydrospiro(4H-indene-1,2'-oxirane) (Compound 9) (part 2)

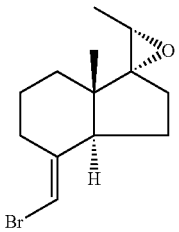

Under a nitrogen atmosphere, a solution of (1Z,3aR,4E,7aS)-4-(bromomethylene)-1-ethylidene-octahydro-7a-methyl-1H-indene (Compound 20: 22.4 mg, 0.08778 mmol) in ethyl acetate (0.4 ml) was cooled in an ice bath, and meta-chloroperbenzoic acid (65%, 23.3 mg, 0.08778 mmol) was added thereto. After stirring the reaction mixture at the same temperature for 1 hour, sodium hydrogen carbonate (7 mg, 0.08778 mmol), saturated aqueous sodium thiosulfate solution (0.5 ml), water (0.5 ml) and saturated aqueous sodium hydrogen carbonate solution (0.5 ml) were added thereto, and the resulting mixture was extracted twice with ethyl acetate. The organic layer was washed with saturated aqueous sodium hydrogen carbonate solution (2.5 ml) and saturated brine (2.5 ml), and dried over sodium sulfate, followed by evaporation under reduced pressure. The obtained crude product (24.6 mg) was purified by flash column chromatography to obtain (E,1R,3aR,7aS,3'S)-3',7a-dimethyl-4-(bromomethylene)octahydrospiro(4H-indene-1,2'-oxirane) (18.6 mg, 78.2%). The spectrum data thereof agreed with the data described in Example 3.

Example 19

Synthesis of (1E,3aR,4E,7aS)-4-(bromomethylene)-1-ethylidene-octahydro-7a-methyl-1H-indene (Compound 21)

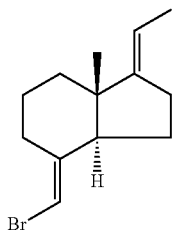

Under a nitrogen atmosphere, a solution of (S)-1-{(E,3S,3aS,7aR)-7-(bromomethylene)-octahydro-3a-methyl-1H-indene-3-yl}ethanol (Compound 18: 52.4 mg, 0.1918 mmol) and triphenylphosphine (126 mg, 0.4795 mmol) in tetrahydrofuran (0.3 ml) was cooled in an ice bath, and azodicarboxylic acid diethyl ester (2.2 M in toluene, 223.4 μl, 0.4915 mmol) was added dropwise thereto. The reaction mixture was stirred in the ice bath for 10 minutes and at room temperature for 21 hours, and then evaporated under reduced pressure.

The obtained crude product was purified by flash column chromatography to obtain (1E,3aR,4E,7aS)-4-(bromomethylene)-1-ethylidene-octahydro-7a-methyl-1H-indene (21.8 mg, 44.6%).

$^1$H NMR (CDCl$_3$) δ: 5.69 (1H, bs), 5.00-5.20 (1H, m), 2.80-3.00 (1H, m), 2.15-2.45 (2H, m), 1.90-2.05 (1H, m), 1.50-1.90 (6H, m), 1.56 (3H, dt, J=6.8, 1.5 Hz), 1.2-1.45 (1H, m), 0.64 (3H, s)

Rf value (silica gel plate, developing solvent; hexane): 0.6

Example 20

Synthesis of (E,1R,3aR,7aS)-4-(bromomethylene)-octahydro-1-{(R)-1-hydroxyethyl}-7a-methyl-1H-indene-1-ol (Compound 22)

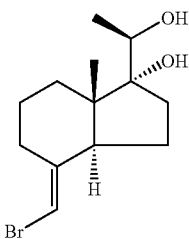

To a mixture of (1E,3aR,4E,7aS)-4-(bromomethylene)-1-ethylidene-octahydro-7a-methyl-1H-indene (Compound 21: 19.2 mg, 0.07524 mmol), methanesulfonamide (21.5 mg, 0.2257 mmol) and AD-mix-α (105 mg), t-butanol (0.4 ml) and water (0.4 ml) were added, and the reaction mixture was stirred at room temperature for 48 hours. Sodium sulfite (113 mg) was added thereto and the resulting mixture was stirred at room temperature for 1 hour. Ethyl acetate and water were added thereto, and the resulting mixture was extracted 3 times with ethyl acetate. The organic layer was washed with 2 M aqueous potassium hydroxide solution (1 ml) and saturated brine (2.5 ml), and dried over sodium sulfate, followed by evaporation under reduced pressure. The obtained crude product (23.2 mg) was purified by flash column chromatography to obtain (E,1R,3aR,7aS)-4-(bromomethylene)-octahydro-1-{(R)-1-hydroxyethyl}-7a-methyl-1H-indene-1-ol (18.6 mg, 85.3%).

$^1$H NMR (CDCl$_3$) δ: 5.65 (1H, bs), 3.90-4.10 (1H, m), 2.80-3.00 (1H, m), 2.60-2.75 (1H, m), 2.14 (1H, s), 1.40-1.80 (9H, m), 1.36 (1H, d, J=5.0 Hz), 1.19 (3H, d, J=6.4 Hz), 0.69 (3H, s)

Rf value (silica gel plate, developing solvent; hexane:ethyl acetate=3:1): 0.2

Example 21

Synthesis of (E,1R,3aR,7aS,3'S)-3',7a-dimethyl-4-(bromomethylene)octahydrospiro(4H-indene-1,2'-oxirane) (Compound 9) (part 3)

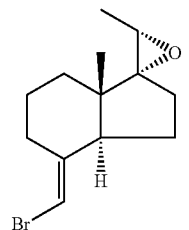

Under a nitrogen atmosphere, a solution of (E,1R,3aR,7aS)-4-(bromomethylene)-octahydro-1-{(R)-1-hydroxyethyl}-7a-methyl-1H-indene-1-ol (Compound 22: 17.8 mg, 0.06155 mmol) in methylene chloride (0.7 ml) was cooled in an ice bath, and triethylamine (43 μl, 0.3078 mmol) was added thereto. Methanesulfonyl chloride (5.7 μl, 0.7386 mmol) was added dropwise thereto, and the reaction mixture was stirred in the ice bath for 15 hours and 45 minutes, followed by adding water (1 ml) thereto. The reaction mixture was extracted twice with ethyl acetate. The combined organic layer was washed with saturated brine (2.5 ml) and dried over sodium sulfate, followed by evaporation under reduced pressure. The obtained crude product (22.5 mg) was dissolved in tetrahydrofuran (0.4 ml) under a nitrogen atmosphere, and the resulting mixture was cooled in an ice bath. Sodium methoxide (1.0 M in methanol, 154 μl, 0.1539 mmol) was added dropwise thereto, and the reaction mixture was stirred at the same temperature for 25 minutes. Water (1 ml) was added thereto, and the resulting mixture was extracted twice with ethyl acetate. The organic layer was washed with saturated brine (2.5 ml), dried over sodium sulfate and then evaporated under reduced pressure. The obtained crude product (16.6 mg) was purified by flash column chromatography to obtain (E,1R,3aR,7aS,3'S)-3',7a-dimethyl-4-(bromomethylene)octahydrospiro(4H-indene-1,2'-oxirane) (13.5 mg, 80.8%). The spectrum data thereof agreed with the data described in Example 3.

Example 22

Synthesis of (E)-(4'aR,8'aS)-8'-bromomethylene-4'a-methyl-octahydro-spiro{[1,3]dioxolane-2,2'-naphthalene} (Compound 24)

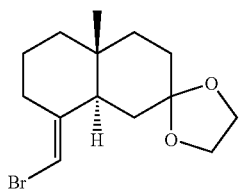

Under a nitrogen atmosphere, to a suspension of bromomethyltriphenylphosphonium bromide (28.5 g, 65.3 mmol) in toluene (100 ml), potassium hexamethyldisilazide (0.5 M in toluene, 85 ml, 42.5 mmol) was added dropwise at 0° C. After stirring the resulting mixture for 15 minutes, the mixture was allowed to rise to room temperature and sonicated for 5 minutes. A solution in toluene (10 ml) of (4'aR,8'aS)-4'a-methyl-octahydro-spiro{[1,3]dioxolane-2,2'-naphthalene}-8'-one (Compound 23: 3.26 g, 14.5 mmol) synthesized in accordance with the method described in the literature (J. Org. Chem. 1966, 31, 2933-2941) was added thereto. 10 ml of toluene was used to rinse a flask from which the solution was removed, and the rinsing was also added to the mixture. The reaction solution was heated to 30° C. and stirred for 17.5 hours. To the reaction solution, 400 ml hexane was added, and the precipitates were removed by filtration. The filtrate was evaporated, and saturated aqueous ammonium chloride solution was added thereto. The resulting mixture was extracted with hexane. The organic layer was washed with saturated brine (5 ml), dried over sodium sulfate and then evaporated under reduced pressure. The crude product was purified by flash column chromatography to obtain (E)-(4'aR,8'aS)-8'-bromomethylene-4'a-methyl-octahydro-spiro{[1,3]dioxolane-2,2'-naphthalene} (2.58 g, 59.0%).

$^1$H NMR (CDCl$_3$) δ: 5.58 (t, J=1.5 Hz, 1H), 3.85-4.00 (m, 4H), 2.97 (ddt, J=13.2 Hz, 1.8 Hz, 1.8 Hz, 1H), 2.19 (ddd, J=10.8 Hz, 5.4 Hz, 1.8 Hz, 1H), 1.35-1.85 (m, 10H), 1.35 (dd, J=13.2 Hz, 4.8 Hz, 1H), 0.74 (s, 3H)

Rf value (silica gel plate, developing solvent; hexane:ethyl acetate=3:1): 0.6

Example 23

Synthesis of (E,4aR,8aR)-8-(bromomethylene)-octahydro-4-a-methylnaphthalene-2(1H)-one (Compound 25)

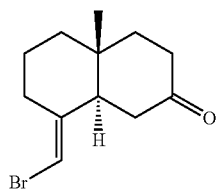

(E)-(4'aR,8'aS)-8'-bromomethylene-4'a-methyl-octahydro-spiro[[1,3]dioxolane-2,2'-naphthalene] (Compound 24: 2.43 g, 8.07 mmol) was dissolved in acetic acid (40 ml), and water (10 ml) was added thereto. The reaction solution was heated to 80° C. and stirred for 1 hour. After cooling to room temperature, the reaction solution was added to 200 ml water, and the resulting mixture was extracted with ethyl acetate. The organic layer was washed with 2 N aqueous sodium hydroxide solution and further with saturated brine. The organic layer was dried over sodium sulfate and evaporated under reduced pressure. The obtained crude product (2.00 g) was purified by flash column chromatography to obtain (E,4aR,8aR)-8-(bromomethylene)-octahydro-4a-methylnaphthalene-2(1H)-one (1.86 g, 89.9%).

$^1$H NMR (CDCl$_3$) δ: 5.63 (t, J=1.2 Hz, 1H), 2.95-3.10 (m, 1H), 2.48 (td, J=14.1 Hz, 8.8 Hz, 1H), 2.20-2.40 (m, 4H), 1.50-1.85 (m, 6H), 1.30-1.40 (m, 1H), 0.94 (s, 3H)

Rf value (silica gel plate, developing solvent; hexane:ethyl acetate=5:1): 0.3

Example 24

Synthesis of (4aR,8E,8aR)-8-(bromomethylene)-4a,5,6,7,8,8a-hexahydro-4a-methylnaphthalene-2(1H)-one (Compound 26)

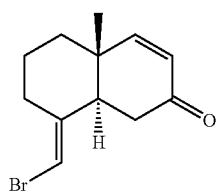

To a solution of ortho-iodoxybenzoic acid (1.56 g, 5.57 mmol) in dimethyl sulfoxide (17 ml), (E,4aR,8aR)-8-(bromomethylene)-octahydro-4a-methylnaphthalene-2(1H)-one (Compound 25: 955 mg, 3.71 mmol) was added, and the resulting mixture was stirred at 80° C. for 18 hours. The resulting mixture was cooled to room temperature, and 5% aqueous sodium hydrogen carbonate solution was added thereto. The resulting mixture was extracted with diethyl ether, and the organic layer was washed with water and saturated brine. Further, the combined aqueous layer was extracted with ethyl acetate which was then washed with water and saturated brine. The combined organic layer was dried over sodium sulfate and evaporated under reduced pressure. The obtained crude product (976 mg) was purified by flash column chromatography to obtain (4aR,8E,8aR)-8-(bromomethylene)-4a,5,6,7,8,8a-hexahydro-4a-methylnaphthalene-2(1H)-one (443 mg, 46.8%). $^1$H NMR (CDCl$_3$) δ: 6.76 (d, J=9.9 Hz, 1H), 5.88 (d, J=9.9 Hz, 1H), 5.74 (t, J=1.5 Hz, 1H), 2.95-3.10 (m, 1H), 2.66 (ddd, J=11.7 Hz, 5.7 Hz, 1.5 Hz, 1H), 2.45 (d, J=12.0 Hz, 1H), 2.43 (d, J=6 Hz, 1H), 1.50-1.90 (m, 5H), 0.98 (s, 3H)

Example 25

Synthesis of (1Z,3aR,4E,7aS)-4-(bromomethylene)-hexahydro-7a-methyl-1-{(phenylamino)methylene}-1H-indene-2(3H)-one (Compound 27)

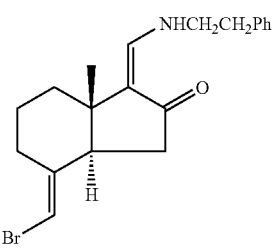

To a solution of (4aR,8E,8aR)-8-(bromomethylene)-4a,5,6,7,8,8a-hexahydro-4a-methylnaphthalene-2(1H)-one (Compound 26: 301 mg, 1.18 mmol) in methylene chloride (3 ml), phenethyl azide (257 mg, 1.75 mmol) and trimethylsilyl trifluoromethanesulfonate (225 μl, 1.24 mmol) were added at 0° C., and the resulting mixture was stirred for 6 hours. Saturated aqueous sodium bicarbonate was added to the reaction solution, and the organic layer was separated. The aqueous layer was extracted with methylene chloride, and the combined organic layer was washed with saturated brine and dried over magnesium sulfate, followed by evaporation under reduced pressure to obtain a crude product (638 mg). The crude product was purified by flash column chromatography to obtain (1Z,3aR,4E,7aS)-4-(bromomethylene)-hexahydro-7a-methyl-1-{(phenylamino)methylene}-1H-indene-2(3H)-one (374 mg, 85%).

$^1$H NMR (CDCl$_3$) δ: 8.63 (dt, J=12.0 Hz, 6.0 Hz, 1H), 7.10-7.40 (m, 5H), 6.16 (d, J=12.6 Hz, 1H), 5.70 (s, 1H), 3.41 (dt, J=6.9 Hz, 6.9 Hz, 2H), 2.85-3.00 (m, 1H), 2.84 (t, J=6.9 Hz, 2H), 2.38 (s, 1H), 2.37 (dd, J=20.7 Hz, 13.5 Hz, 1H), 2.07 (dd, J=22.2 Hz, 12.9 Hz, 1H), 1.50-1.90 (m, 4H), 1.30-1.45 (m, 1H), 0.78 (s, 3H)

Rf value (silica gel plate, developing solvent; hexane:ethyl acetate=3:1): 0.2

Example 26

Synthesis of N-[(1Z)-{(E,3aS,7aR)-7-(bromomethylene)-octahydro-3a-methyl-2-oxoindene-3-ylidene}methyl]-N-phenethylacetamide (Compound 28)

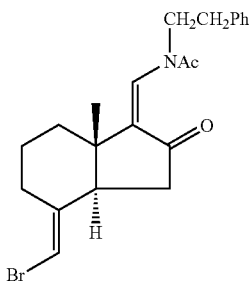

To a solution of (1Z,3aR,4E,7aS)-4-(bromomethylene)-hexahydro-7a-methyl-1-{(phenylamino)methylene}-1H-indene-2(3H)-one (Compound 27: 182 mg, 0.486 mmol) in pyridine (1 ml), acetyl chloride (50 μl, 0.703 mmol) was added at 0° C. The resulting mixture was allowed to rise to room temperature and stirred for 30 minutes. The solvent was removed by evaporator, and the residue was dissolved in diethyl ether. The resulting mixture was washed with 2 N hydrochloric acid, water and with saturated brine, and dried over magnesium sulfate, followed by evaporation under reduced pressure to obtain a crude product of N-[(1Z)-{(E,3aS,7aR)-7-(bromomethylene)-octahydro-3a-methyl-2-oxoindene-3-ylidene}methyl]-N-phenethylacetamide (184 mg, 91%).

$^1$H NMR (CDCl$_3$) δ: 7.05-7.35 (m, 5H), 6.00-6.40 (brs, 1H), 5.71 (s, 1H), 4.20-4.40 (m, 1H), 3.85-4.05 (m, 1H), 2.90-3.05 (m, 1H), 2.82 (t, J=6.9 Hz, 2H), 1.95-2.50 (m, 3H), 2.11 (s, 3H), 1.60-2.00 (m, 4H), 1.37 (m, 1H), 0.82 (s, 3H)

Rf value (silica gel plate, developing solvent; hexane:ethyl acetate=3:1): 0.2

Example 27

Synthesis of (3aR,4E,7aS)-4-(bromomethylene)-3a,4,5,6,7,7a-hexahydro-7a-methyl-3H-indene-1-carbaldehyde (Compound 29)

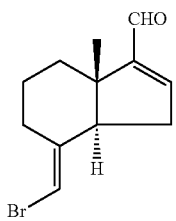

The crude product of N-[(1Z)-{(E,3aS,7aR)-7-(bromomethylene)-octahydro-3a-methyl-2-oxoindene-3-ylidene}methyl]-N-phenethylacetamide (Compound 28) (178 mg, 0.428 mmol) was dissolved in methanol (2 ml), and sodium borohydride (20 mg, 0.529 mmol) was added thereto at 0° C. After stirring the resulting mixture for 10 minutes, the solvent was removed by evaporator. The residue was dissolved in ethyl acetate, and the resulting mixture was passed through a small amount of silica gel to obtain a crude product (154 mg). The obtained crude product (146 mg, 0.349 mmol) was dissolved in tetrahydrofuran (2 ml), and 2 N sulfuric acid (0.5 ml) was added thereto. The resulting mixture was heated to 70° C. and stirred for 4.5 hours. After cooling, the reaction solution was diluted with diethyl ether, and water was added thereto. The resulting mixture was extracted with diethyl ether. The combined organic layer was washed with saturated aqueous sodium hydrogen carbonate and with saturated brine, dried over magnesium sulfate, and evaporated under reduced pressure to obtain a crude product (140 mg). The crude product was purified by flash column chromatography to obtain (3aR,4E,7aS)-4-(bromomethylene)-3a,4,5,6,7,7a-hexahydro-7a-methyl-3H-indene-1-carbaldehyde (84 mg, 94%).

$^1$H NMR (CDCl$_3$) δ: 9.71 (s, 1H), 6.79 (t, J=2.7 Hz, 1H), 5.77 (t, J=1.8 Hz, 1H), 2.80-2.95 (m, 1H), 2.30-2.60 (m, 4H), 1.70-1.90 (m, 3H), 1.45-1.65 (m, 1H), 0.83 (s, 3H)

Rf value (silica gel plate, developing solvent; hexane:ethyl acetate=4:1): 0.4

Example 28

Synthesis of (S)-1-{(3aS,7E,7aR)-7-(bromomethylene)-3a,4,5,6,7,7a-hexahydro-3a-methyl-1H-indene-3-yl}ethanol (Compound 5) (part 3)

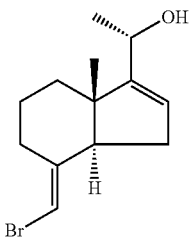

(1R)-trans-N,N'-1,2-cyclohexanediylbis(1,1,1-trifluoromethanesulfonamide) (2.3 mg, 0.006 mmol) was placed in a reaction vessel. After replacing the atmosphere with nitrogen, t-butyl methyl ether (0.03 ml) was added thereto and dissolved. To the solution, tetraisopropoxy titanium (0.0177 ml, 0.06 mmol) was added at room temperature, and the resulting mixture was heated at 50° C. for 30 minutes. After cooling to room temperature, dimethylzinc (1.0 M in heptane, 0.12 ml, 0.12 mmol) was added thereto. The obtained reaction mixture was added to (3aR,4E,7aS)-4-(bromomethylene)-3a,4,5,6,7,7a-hexahydro-7a-methyl-3H-indene-1-carbaldehyde (Compound 29: 15.3 mg, 0.06 mmol). After stirring the reaction solution at room temperature for 1 hour, ethyl acetate (30 ml) was added thereto, and the resulting mixture was washed with 2N hydrochloric acid, saturated brine and with saturated aqueous sodium hydrogen carbonate solution, respectively. The organic layer was dried over sodium sulfate, and the solvent was evaporated to obtain the reaction mixture. The reaction mixture was purified by preparative TCL to obtain (S)-1-{(3aS,7E,7aR)-7-(bromomethylene)-3a,4,5,6,7,7a-hexahydro-3a-methyl-1H-indene-3-yl}ethanol (18.4 mg, 100%). The spectrum data thereof agreed with the data described in Example 4.

Example 29

Synthesis of [{(5Z,7E)-(1S,3R,20S)-1,3-bis(t-butyldimethylsilyloxy)-9,10-secopregna-5,7,10(19),16-tetraen-20-yl}oxy]-N-(2,2,3,3,3-pentafluoropropyl)acetamide (compound represented by Formula (4))

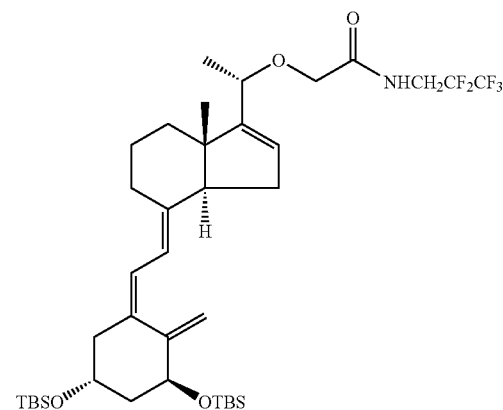

2-[(S)-1-{(3aS,7E,7aR)-7-(bromomethylene)-3a,4,5,6,7,7a-hexahydro-3a-methyl-1H-indene-3-yl}ethoxy]-N-(2,2,3,3,3-pentafluoropropyl)acetamide (Compound 2: 400 mg, 0.87 mmol), palladium acetate (19.6 mg, 0.087 mmol) and triphenylphosphine (137 mg, 0.52 mmol) were dissolved in toluene (3.3 ml), and (3S,5R)-3,5-bis(t-butyldimethylsilyloxy)octa-1-en-7-yne (480 mg, 1.3 mmol) synthesized in accordance with the method described in Tetrahedron Lett. 1994, 35, 8119-8122 was added thereto, followed by replacing the atmosphere in the reaction vessel with nitrogen. Triethylamine (1.7 ml, 12.2 mmol) was added thereto, and the atmosphere in the reaction vessel was replaced again with nitrogen. The reaction mixture was heated to 90° C. and stirred for 9 hours. After cooling the reaction mixture to room temperature, t-butyl methyl ether (4 ml) and 5% hydrogen peroxide solution (4 ml) were added thereto, and the resulting mixture was stirred at room temperature for 30 minutes, followed by separating the solution. The obtained organic layer was washed with aqueous sodium thiosulfate solution (4 ml), and dried over magnesium sulfate. The solvent was evaporated under reduced pressure. Hexane (4 ml) was added to the obtained mixture, and insoluble matters were removed, followed by evaporation of the organic solvent to obtain the reaction mixture. The obtained crude product was purified by silica gel column chromatography to obtain [{(5Z,7E)-(1S,3R,20S)-1,3-bis(t-butyldimethylsilyloxy)-9,10-secopregna-5,7,10(19),16-tetraen-20-yl}oxy]-N-(2,2,3,3,3-pentafluoropropyl)acetamide (379 mg).

$^1$H NMR (CDCl$_3$) δ: 0.06-0.08 (m, 12H), 0.78 (s, 3H), 0.88 (s, 9H), 0.89 (s, 9H), 1.37 (d, J=6.6 Hz, 3H), 1.40-2.52 (m, 12H), 2.76-2.88 (m, 1H), 3.86 (d, J=15.6 Hz, 1H), 3.93-4.08 (m, 4H), 4.14-4.27 (m, 1H), 4.38 (dd, J=3.7, 6.4 Hz, 1H), 4.87 (d, J=2.1 Hz, 1H), 5.19 (dd, J=1.0, 2.6 Hz, 1H), 5.60 (br, 1H), 6.10 (d, J=11.5 Hz, 1H), 6.23 (d, J=11.5 Hz, 1H), 6.91 (br, 1H)

Rf value (silica gel plate, developing solvent; hexane:ethyl acetate=3:1): 0.6

Example 30

Synthesis of [{(5Z,7E)-(1S,3R,20S)-1,3-dihydroxy-9,10-secopregna-5,7,10(19),16-tetraen-20-yl}oxy]-N-(2,2,3,3,3-pentafluoropropyl)acetamide (Compound 1)

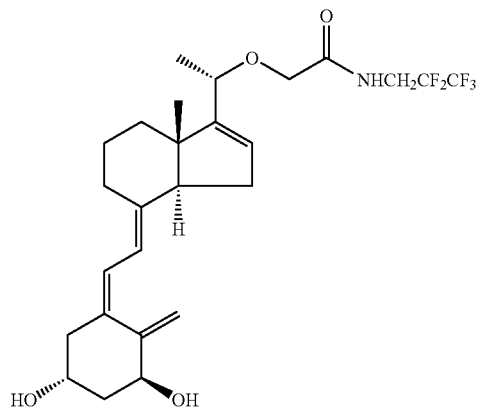

To [{(5Z,7E)-(1S,3R,20S)-1,3-bis(t-butyldimethylsilyloxy)-9,10-secopregna-5,7,10(19),16-tetraen-20-yl}oxy]-N-(2,2,3,3,3-pentafluoropropyl)acetamide (338 mg, 0.519 mmol), hydrochloric acid solution in ethanol (containing 1.5% hydrochloric acid, 3.4 ml) was added, and the resulting mixture was stirred at room temperature for 4 hours. Triethylamine (0.163 ml) was added to the reaction solution, and the solvent was evaporated under reduced pressure. To the resulting product, t-butyl methyl ether (3.4 ml) and 20% brine (3.4 ml) were added, and the solution was separated. The obtained organic layer was dried over magnesium sulfate, and the solvent was evaporated to obtain a crude product. The crude product was purified by silica gel column chromatography to obtain [{(5Z,7E)-(1S,3R,20S)-1,3-dihydroxy-9,10-secopregna-5,7,10(19),16-tetraen-20-yl}oxy]-N-(2,2,3,3,3-pentafluoropropyl)acetamide (180 mg).

The NMR data thereof agreed with the data described in Example 22 (2) of WO2001/096293.

[Industrial Applicability]

The process of the present invention does not require any special equipments for photoreaction and is practical. According to the present invention, [{(5Z,7E)-(1S,3R,20S)-1,3-dihydroxy-9,10-secopregna-5,7,10(19),16-tetraen-20-yl}oxy]-N-(2,2,3,3,3-pentafluoropropyl)acetamide, which is useful as a pharmaceutical, can be synthesized efficiently.

The invention claimed is:

1. A process for producing a compound represented by Formula (1):

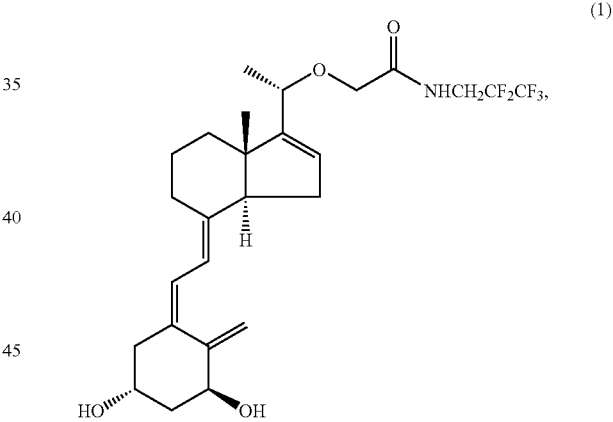

said process comprising the step of reacting a compound represented by Formula (2):

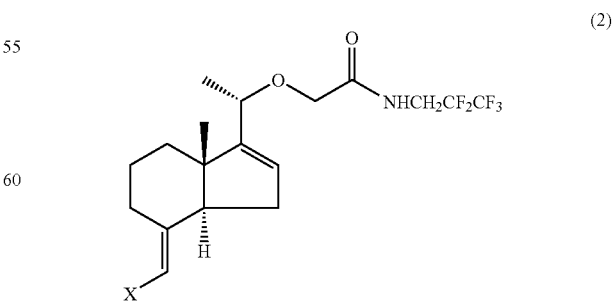

(wherein X represents a halogen atom)

with a compound represented by Formula (3):

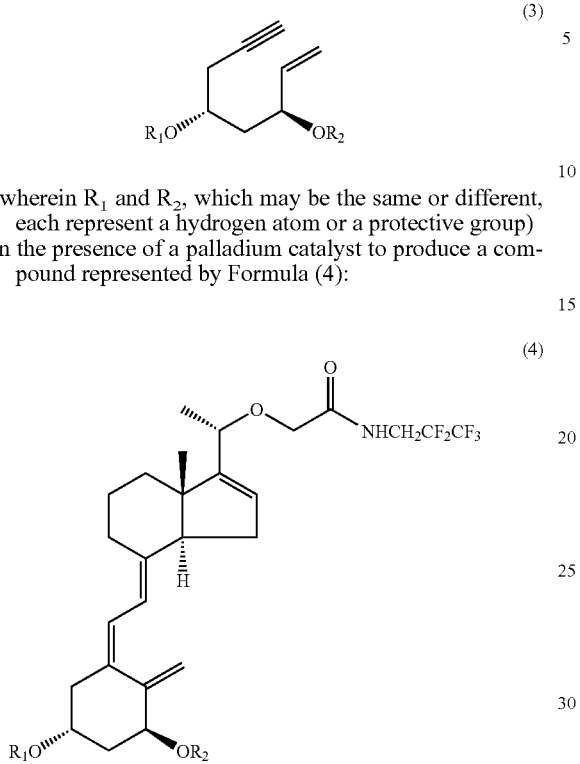

(wherein R₁ and R₂, which may be the same or different, each represent a hydrogen atom or a protective group) in the presence of a palladium catalyst to produce a compound represented by Formula (4):

(wherein $R_1$ and $R_2$ are as defined above).

2. The process according to claim 1, further comprising a step of deprotecting the compound of Formula (4) where $R_1$ and $R_2$ are protective groups.

3. The process according to claim 2, wherein $R_1$ and $R_2$ are simultaneously the same substituted silyl protective group selected from the group consisting of trimethylsilyl group, triethylsilyl group, tri-i-propylsilyl group, dimethyl-i-propylsilyl group, diethyl-i-propylsilyl group, dimethylthexylsilyl group, t-butyldimethylsilyl group, t-butyldiphenylsilyl group, tribenzylsilyl group, tri-p-xylylsilyl group, triphenylsilyl group, diphenylmethylsilyl group, and t-butylmethoxyphenylsilyl group.

4. The process according to claim 3, wherein $R_1$ and $R_2$ are simultaneously t-butyldimethylsilyl group.

5. The process according to claim 3, wherein the deprotection of the compound of Formula (4) is carried out in the presence of an acid.

6. The process according to claim 5, wherein said acid is hydrochloric acid.

7. The process according to claim 1, wherein X is a bromine atom.

8. A compound represented by Formula (2):

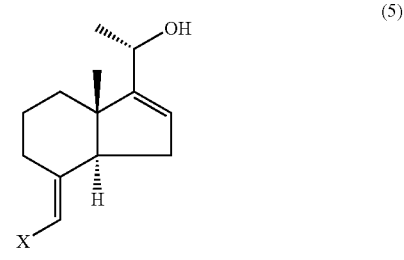

(wherein X represents a halogen atom).

9. A process for producing a compound claimed in claim 8, comprising the step of reacting a compound represented by Formula (5):

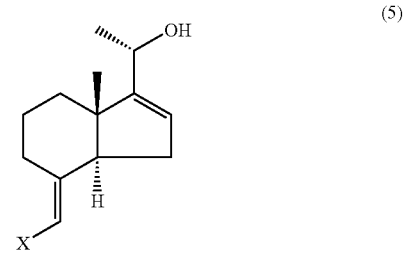

(wherein X represents a halogen atom) with 2-bromo-N-(2,2,3,3,3-pentafluoropropyl)acetamide in the presence of a base.

10. The process according to claim 9, wherein the reaction is carried out in N,N-dimethylformamide.

11. A compound represented by Formula (5):

(wherein X represents a halogen atom).

* * * * *